United States Patent [19]

Degnan et al.

[11] Patent Number: 5,191,148
[45] Date of Patent: Mar. 2, 1993

[54] ISOPARAFFIN/OLEFIN ALKYLATION

[75] Inventors: Thomas F. Degnan, Moorestown; Kenneth J. Del Rossi, Woodbury, both of N.J.; Albin Huss, Jr., Chadds Ford, Pa.

[73] Assignee: Mobil Oil Corporation, Fairfax, Va.

[21] Appl. No.: 696,484

[22] Filed: May 6, 1991

[51] Int. Cl.$^5$ .............................................. C07C 2/58
[52] U.S. Cl. ................................. 585/724; 585/722; 585/726
[58] Field of Search ................ 585/722, 723, 724, 725, 585/726

[56] References Cited

U.S. PATENT DOCUMENTS

| | | | |
|---|---|---|---|
| 2,804,491 | 8/1957 | May et al. | 260/683.4 |
| 3,236,671 | 2/1966 | Dybalski et al. | 106/277 |
| 3,251,902 | 5/1966 | Garwood et al. | 260/683.64 |
| 3,450,644 | 6/1969 | Lanewala et al. | 252/416 |
| 3,467,728 | 9/1969 | Hervert | 260/683.2 |
| 3,549,557 | 12/1970 | Bolton et al. | 252/455 |
| 3,644,565 | 2/1972 | Biale | 260/683.43 |
| 3,647,916 | 3/1972 | Caesar et al. | 260/683.43 |
| 3,655,813 | 4/1972 | Kirsch et al. | 260/683.43 |
| 3,706,814 | 12/1972 | Kirsch et al. | 260/683.43 |
| 3,738,977 | 6/1973 | Biale | 260/94.9 |
| 3,800,003 | 3/1974 | Sobel | 260/683.49 |
| 3,862,258 | 1/1975 | Huang et al. | 260/683.44 |
| 3,917,738 | 11/1975 | Fenske et al. | 260/683.43 |
| 3,977,621 | 8/1976 | Huffman | 242/75.5 |
| 4,176,090 | 11/1979 | Vaughan et al. | 252/455 Z |
| 4,216,188 | 8/1980 | Shabrai et al. | 423/118 |
| 4,248,739 | 2/1981 | Vaughan et al. | 252/455 R |
| 4,308,414 | 12/1981 | Madgavkar et al. | 585/525 |
| 4,365,105 | 12/1982 | Morganson et al. | 585/525 |
| 4,367,163 | 1/1983 | Pinnavaia et al. | 252/455 R |
| 4,384,161 | 5/1983 | Huang | 585/722 |
| 4,429,177 | 1/1984 | Morganson et al. | 585/525 |
| 4,440,871 | 4/1984 | Lok et al. | 502/214 |
| 4,619,818 | 10/1986 | Derouane et al. | 423/306 |
| 4,623,527 | 11/1986 | Derouane et al. | 423/306 |
| 4,632,811 | 12/1986 | Derouane et al. | 423/306 |
| 4,639,358 | 1/1987 | Derouane et al. | 423/306 |
| 4,647,442 | 3/1987 | Derouane et al. | 423/306 |
| 4,664,897 | 5/1987 | Derouane et al. | 423/306 |
| 4,673,559 | 6/1987 | Derouane et al. | 423/306 |
| 4,713,227 | 12/1987 | Derouane et al. | 423/305 |
| 4,831,006 | 5/1989 | Aufdembrink | 502/242 |
| 4,859,648 | 8/1989 | Landis et al. | 502/242 |
| 5,012,033 | 4/1991 | Child et al. | 585/722 |
| 5,057,296 | 10/1991 | Beck | 423/277 |

OTHER PUBLICATIONS

"Fixed Bed Catalytic Process to Produce Synthetic Lubricants from Decene-1", *Ind. Eng. Chem. Prod. Res. Dev.*, 22, (1983).

"Modern Alkylation", Lyle F. Albright, *Oil and Gas Journal*, Nov. 12 & 26, 1990.

*Kirk-Othmer Encyclopedia of Chemical Technology*, 3rd Ed., vol. 20, John Wiley & Sons, New York, pp. 766–781, 1982.

"Oxides and Hydroxides of Aluminum", Technical Paper No. 19 Revised, Alcoa Research labs, pp. 54–59, 1987.

*Primary Examiner*—Asok Pal
*Attorney, Agent, or Firm*—Alexander J. McKillop; Dennis P. Santini; Robert B. Furr, Jr.

[57] ABSTRACT

The present invention provides a process for alkylating an isoparaffin with an olefin comprising contacting an isoparaffin having from 4 to 8 carbon atoms with an olefin having from 2 to 12 carbon atoms in an alkylation reaction zone at temperature from about −20° C. to about 150° C. with an alkylation catalyst complex comprising a Lewis acid and an inorganic, porous crystalline phase material having, after calcination, a d-spacing greater than about 18 Angstrom Units and having a benzene adsorption capacity of greater than 15 grams benzene per 100 grams of said material at 50 torr and 25° C., wherein the molar ratio of said isoparaffin to said olefin is from about 1 to about 250 to evolve a product stream containing C$_5$+alkylate. In a preferred embodiment, the alkylation catalyst complex comprises a Lewis acid and an inorganic, porous crystalline phase material having, after calcination, a hexagonal arrangement of uniformly-sized pores having diameters of at least about 13 Angstrom Units and exhibiting a hexagonal electron diffraction pattern that can be indexed with a d$_{100}$ value greater than about 18 Angstrom Units.

55 Claims, 21 Drawing Sheets

ISOPARAFFIN/OLEFIN ALKYLATION

FIELD OF THE INVENTION

The present invention relates to the art of improving octane rating of gasoline by alkylating an isoparaffin with an olefin stream in the presence of a Lewis acid-promoted catalyst comprising an ultra-large pore synthetic crystalline material to provide an alkylate product useful as a high octane blending component in gasoline.

BACKGROUND OF THE INVENTION

This invention results from a need to improve octane ratings for gasoline. Isoparaffin-olefin alkylation is a means to produce highly branched paraffins which effects this octane improvement.

Alkylation is a reaction in which an alkyl group is added to an organic molecule. Thus, an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This is a very valuable blending component in the manufacture of gasolines because of its high octane rating.

Traditionally, the process in the industry includes the use of hydrofluoric acid or sulfuric acid and a catalysis carried out under controlled temperature conditions. Low temperatures are utilized in the sulfuric acid process to minimize the side reaction of olefin polymerization and the acid strength is generally maintained at 88 to 94% by the continuous addition of fresh acid and the continuous withdrawal of spent acid. The hydrofluoric acid process is less temperature-sensitive and the acid is easily recovered and purified.

The typical types of alkylation currently used to produce high octane blending components, that is, the hydrofluoric acid and sulfuric acid alkylation processes, have inherent drawbacks including environmental concerns, acid consumption and sludge disposal. With the increasing demands for octane and the increasing environmental concerns, it has been desirable to develop an alkylation process based on a catalyst system which can meet product quality demands, while at the same time minimizing safety and environmental problems. Studies to date indicate that Lewis acid-catalyzed alkylation processes have the potential to meet the refiners' requirements for alkylate octane and volumetric production. Examples of Lewis acids include $BF_3$, $AlCl_3$ and $SbF_5$, of which $BF_3$ presently appears to be most promising to catalyze industrial isoparaffin:olefin alkylation. The following references provide an overview of art related to $BF_3$-catalyzed isoparaffin-olefin alkylation.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,450,644 discloses a method for regenerating a zeolite catalyst used in hydrocrabon conversion processes involving carbonium ion intermediates.

U.S. Pat. No. 3,549,557 describes alkylation of isobutane with $C_2$-$C_3$ olefins using certain crystalline aluminosilicate zeolite catalysts in a fixed-, moving- or fluidized-bed system.

U.S. Pat. No. 3,644,565 discloses alkylation of a paraffin with an olefin in the presence of a catalyst comprising a Group VIII noble metal present on a crystalline aluminosilicate zeolite. The catalyst is pretreated with hydrogen to promote selectivity.

U.S. Pat. No. 3,647,916 describes an isoparaffin-olefin alkylation process featuring use of an ion-exchanged crystalline aluminosilicate, isoparaffin/olefin molar ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is used in the alkylation reactor. The isoparaffin and olefin are introduced into the alkylation reactor at specified concentrations and catalyst is continuously regenerated outside the alkylation reactor.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,236,671 discloses an alkylation reaction wherein crystalline aluminosilicate zeolites having silica to alumina mole ratios above 3 are used. The reference also discloses the use of various metals exchanged and/or impregnated on such zeolites.

U.S. Pat. No. 3,624,173 discloses an isoparaffin-olefin alkylation which uses crystalline aluminosilicate zeolites containing gadolinium.

U.S. Pat. No. 3,738,977 discloses alkylation of paraffins with ethylene using a zeolite catalyst which possesses a Group VII metal component. The catalyst is pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone. Thereafter, the reactants are passed concurrently with the catalyst so that a controlled amount of olefin is adsorbed into the catalyst before the combination of reactants and catalyst is introduced into an alkylation zone. This controlled olefin adsorption is thought to prevent polymerization of the olefin during alkyation.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large-pore zeolite with a Lewis acid is reported to increase the activity and selectivity of the zeolite, thereby effecting alkylation with high olefin space velocity and low isoparaffin/olefin ratio.

The article entitled "Fixed Bed Catalytic Process to Produce Synthetic Lubricants from Decene-1", *Ind. Eng. Chem. Prod. Res. Dev.*, 22, (1983), teaches oligomerizing olefins to produce fluids with lubricating properties using a silica-$BF_3$-water catalyst. The authors further teach that with this system much of the $BF_3$ can be recycled to minimize $BF_3$ consumption and disposal problems. The reference teaches that water is a necessary component of the system and that in its absence a BF$_3$-silica catalyst rapidly deactivates. The reference further teaches that for less reactive olefins, such as decene-1, a useful degree of oligomerization is achieved only by adding a measurable quantity of an activator such as water or a primary alcohol to BF$_3$. The authors further point out that other BF$_3$ activators, such as ethers, ketones, acids and anhydrides, are also effective olefin oligomerization catalysts. A commercialized process is reported wherein alkylation of benzene with ethylene, propylene or butenes is achieved by using a BF$_3$-alumina catalyst with BF$_3$ continually added to the feedstock. The article states that the process minimizes both BF$_3$ consumption and disposal problems and further provides a product having excellent lubricating properties. The catalyst is said to require water as an activator.

In U.S. Pat. No. 4,308,414 an olefin, such as 1-decene, is oligomerized in the presence of a three-component catalyst comprising boron trichloride, a minute amount of water and a particulate absorbent material such as silica to a lubricating product predominating in those oligomer fractions having viscosities within the lubricating oil range such as the trimer and tetramer.

U.S. Pat. No. 4,429,177 further relates to a method for making lubricating oil utilizing a catalyst comprising boron trifluoride, a minute amount of elemental oxygen and a particulate absorbent material such as silica. The reference points out that the two-component catalyst comprising a solid absorbent and boron trifluoride gradually loses activity after a period of continued use, which aging cannot be conveniently corrected by increasing the boron trifluoride pressure. As a solution, the reference teaches that this aging can be essentially prevented if a minute amount of elemental oxygen is fed to the reactor.

U.S. Pat. No. 3,997,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105 also relates to oligomerizing an olefin to form lubricating oils in the presence of three-component catalyst which comprises a particular silica absorbent with boron trifluoride and water absorbed on the silica.

U.S. Pat. No. 2,804,491 relates to an isoparaffin/olefin alkylation to make gasoline at temperatures between $-20°$ and $150°$ F. utilizing a two-component catalyst comprising essentially excess BF$_3$ with a "silica stabilized gel alumina". No activators are taught.

In the past, severe activity and stability problems have been noted with respect to zeolite based systems. U.S. Pat. Nos. 3,251,902 and 3,893,942, as well as French Patent 1,593,716, and the article by Kirsh and Potts, *Div. of Pet. Chem. A.C.S.*, 15, A109 (1970), exemplify these problems. Improved stability was noted when a Lewis acid such as BF$_3$ was used in combination with macroreticular acid cation exchange resins as pointed out in U.S. Pat. No. 3,855,342. More recently, U.S. Pat. No. 4,384,161 has disclosed the use of BF$_3$ in combination with large pore zeolites such as ZSM-4 and Beta to effectively catalyze isoparaffin/olefin alkylation reactions.

U.S. Pat. No. 3,467,728 relates to a process for isomerizing olefinic hydrocarbon, such as 1-butene or 1-pentene, by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

The two-part article, "Modern Alkylation", by Lyle F. Albright, *Oil and Gas Journal,* Nov. 12 and 26, 1990, summarizes the state of the art in alkylation technology, and highlights problems associated with various liquid catalyst systems, further emphasizing the desirability of developing a commercially viable isoparaffin:olefin alkylation process employing a promoted solid catalyst.

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100–250 Angstrom particles of dense amorphous silica (*Kirk-Othmer Encyclopedia of Chemical Technology,* 3rd Edition, Vol. 20, John Wiley & Sons, New York, p. 766–781, 1982), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions ( K. Wefers and Chanakya Misra, "Oxides and Hydroxides of Aluminum", Technical Paper No. 19 Revised, Alcoa Research Laboratories, p. 54–59, 1987). Since, in the case of either material, there is no long range order controlling the sizes of pores in the material, the variability in pore size is typically quite high. The sizes of pores in these materials fall into a regime called the mesoporous range, which, for the purposes of this application, is from about 13 to 200 Angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are cross-linked by the sharing of oxygen atoms whereby the ratio of the total Group IIIB element, e.g. aluminum, and Group IVB element, e.g. silicon, atoms to oxygen atoms is 1:2. The electrovalence of the tetrahedra containing the Group IIIB element, e.g. aluminum, is balanced by the inclusion in the crystal of a cation, for example, an alkali metal or an alkaline earth metal cation. This can be expressed wherein the ratio of the Group IIIB element, e.g. aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicate of varying alumina and metal content.

Aluminum phosphates are taught in U.S. Pat. Nos. 4,310,440 and 4,385,994, for example. These aluminum phosphate materials have essentially electroneutral lattices. U.S. Pat. No. 3,801,704 teaches an aluminum phosphate treated in a certain way to impart acidity.

An early reference to a hydrated aluminum phosphate which is crystalline until heated at about 110° C., at which point it becomes amorphous or transforms, is the "$H_1$" phase or hydrate of aluminum phosphate of F.d'Yvoire, *Memoir Presented to the Chemical Society*, No. 392, "Study of Aluminum Phosphate and Trivalent Iron", Jul. 6, 1961 (received), pp. 1762–1776. This material, when crystalline, is identified by the JCPDS International Center for Diffraction Data card number 15-274. Once heated at about 110° C., however, the d'Yvoire material becomes amorphous or transforms to the aluminophosphate form of tridymite.

Compositions comprising crystals having a framework topology after heating at 110° C. or higher giving an X-ray diffraction pattern consistent with a material having pore windows formed by 18 tetrahedral members of about 12-13 Angstroms in diameter are taught in U.S. Pat. No. 4,880,611.

A naturally occurring, highly hydrated basic ferric oxyphosphate mineral, cacoxenite, is reported by Moore and Shen, *Nature*, Vol. 306, No. 5941, pp. 356–358 (1983) to have a framework structure containing very large channels with a calculated free pore diameter of 14.2 Angstroms. R. Szostak et al., *Zeolites: Facts, Figures, Future*, Elsevier Science Publishers B.V., 1989, present work showing cacoxenite as being very hydrophilic, i.e. adsorbing non-polar hydrocarbons only with great difficulty. Their work also shows that thermal treatment of cacoxenite causes an overall decline in X-ray peak intensity.

Silicoaluminophosphates of various structures are taught in U.S. Pat. No. 4,440,871. Aluminosilicates containing phosphorous, i.e. silicoaluminophosphates of particular structures are taught in U.S. Pat. Nos. 3,355,246 (i.e. ZK-21) and 3,791,964 (i.e. ZK-22). Other teachings of silicoaluminophosphates and their synthesis include U.S. Pat. Nos. 4,673,559 (two-phase synthesis method); 4,623,527 (MCM-10); 4,639,358 (MCM-1); 4,647,442 (MCM-2); 4,664,897 (MCM-4); 4,638,357 (MCM-5); and 4,632,811 (MCM-3).

A method for synthesizing crystalline metalloaluminophosphates is shown in U.S. Pat. No. 4,713,227, and an antimonophosphoaluminate and the method for its synthesis are taught in U.S. Pat. No. 4,619,818. U.S. Pat. No. 4,567,029 teaches metalloaluminophosphates, and titaniumaluminophosphate and the method for its synthesis are taught in U.S. Pat. No. 4,500,651.

The phosphorus-substituted zeolites of Canadian Patents 911,416; 911,417; and 911,418 are referred to as "aluminosilicophosphate" zeolites. Some of the phosphorus therein appears to be occluded, not structural.

U.S. Pat. No. 4,363,748 describes a combination of silica and aluminum-calcium-cerium phosphate as a low acid activity catalyst for oxidative dehydrogenation. Great Britain Patent 2,068,253 discloses a combination of silica and aluminum-calcium-tungsten phosphate as a low acid activity catalyst for oxidative dehydrogenation. U.S. Pat. No. 4,228,036 teaches an alumina-aluminum phosphate-silica matrix as an amorphous body to be mixed with zeolite for use as cracking catalyst. U.S. Pat. No. 3,213,035 teaches improving hardness of aluminosilicate catalysts by treatment with phosphoric acid. The catalysts are amorphous.

Other patents teaching aluminum phosphates include U.S. Pat. Nos. 4,365,095; 4,361,705; 4,222,896; 4,210,560; 4,179,358; 4,158,621; 4,071,471; 4,014,945; 3,904,550; and 3,697,550.

The precise crystalline microstructure of most zeolites manifests itself in a well-defined X-ray diffraction pattern that usually contains many sharp maxima and that serves to uniquely define the material. Similarly, the dimensions of pores in these materials are very regular, due to the precise repetition of the crystalline microstructure. All molecular sieves discovered to date have pore sizes in the microporous range, which is usually quoted as 2 to 20 Angstroms, with the largest reported being about 12 Angstroms.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, tritita-nates and perovskites. Another example of a non-water swellable layered material, which can be swollen with certain organic swelling agents, is a vacancy-containing titanometallate material, as described in U.S. Pat. No. ent 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle reqion on the X-ray diffraction pattern is observed, at a d-spacing corresponding to the interlayer repeat in the pillared material. Less disrupted materials may show several peaks in this region that ar generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

Each of the preceeding references is incorporated by reference a if set forth at length herein.

SUMMARY OF THE INVENTION

The present invention provides an isoparaffin:olefin alkylation process conducted in the presence of a catalyst complex comprising a Lewis acid promoted ultra-large pore synthetic crystalline material as further described herein.

The invention therefore includes a process for alkylating an isoparaffin with an olefin comprising contacting an isoparaffin having from 4 to 8 carbon atoms with an olefin having from 2 to 12 carbon atoms in an alkylation reaction zone at temperature from about $-40°$ C. to about $200°$ C. with an alkylation catalyst complex comprising a Lewis acid and an inorganic, porous crystalline phase material having, after calcination, a hexagonal arrangement of uniformly-sized pores having diameters of at least about 13 Angstrom Units and exhibiting a hexagonal electron diffraction pattern that can be indexed with a $d_{100}$ value greater than about 18 Angstrom Units, wherein the overall molar feed ratio of said isoparaffin to said olefin is from about 1:1 to about 250:1 to evolve a product stream containing $C_5+$ alkylate.

DETAILED DESCRIPTION

Figure 1:
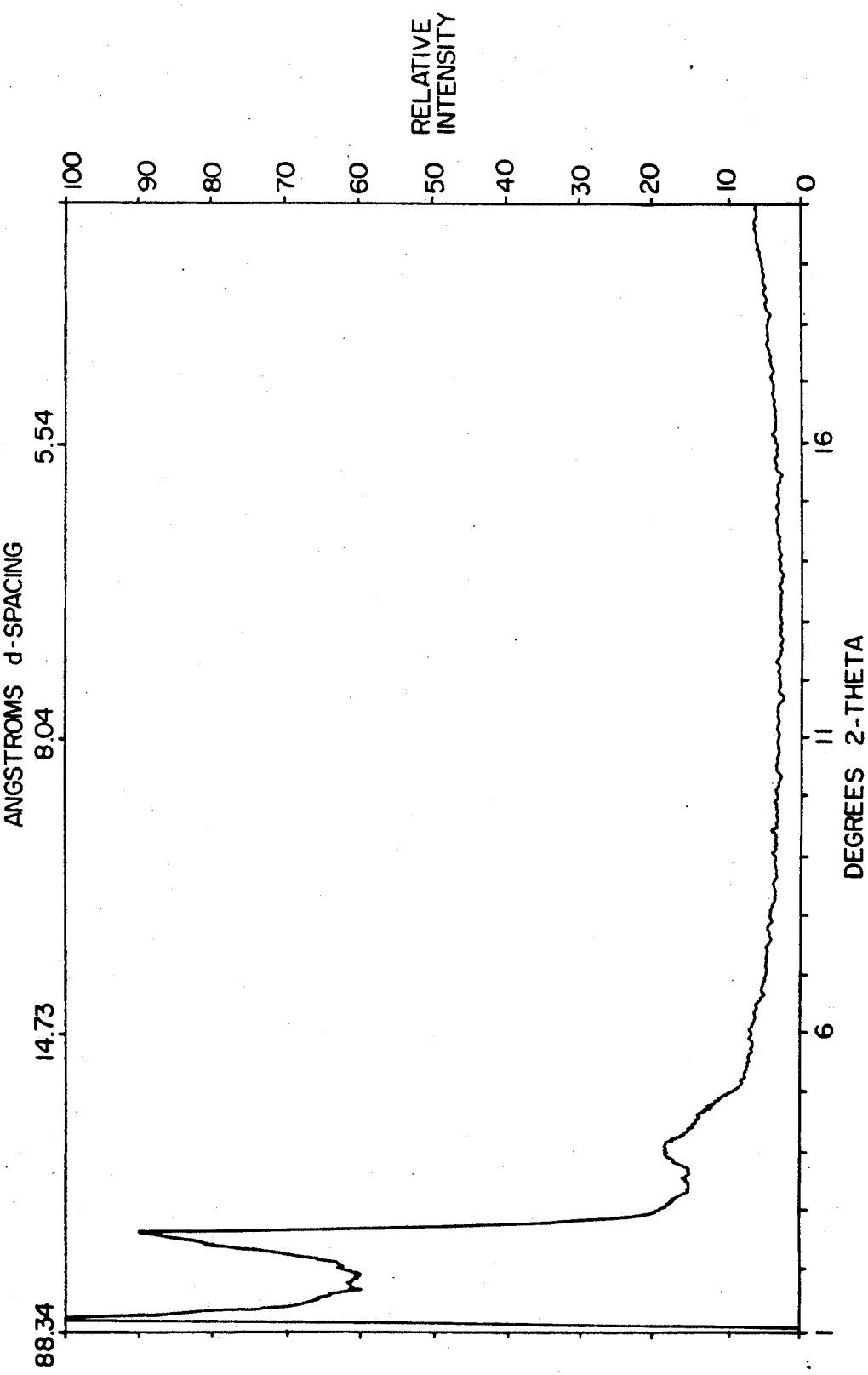
FIGS. 1-15 are X-ray diffraction patterns of products of Examples 1-14 and 16, respectively, hereinafter presented.

Alkylate is a particularly valuable portion of the gasoline pool, as it has both high research and motor octane, contains no olefins or aromatics and little or no sulfur, demonstrates excellent stability, and is clean burning. The present process, therefore, not only produces a superior motor fuel blending component, but also improves refinery safety and reliability while minimizing environmental concerns historically associated with the manufacture of alkylate gasolines.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the C olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44-56, the disclosure of which is incorporated by reference as if set forth at length herein.

The molar ratio of isoparaffin to olefin is generally from about 1:1 to about 250:1, preferably from about 1:1 to about 50:1, and more preferably from about 5:1 to about 25:1.

Process Conditions

The present alkylation process is suitably conducted at temperatures of from about −40° to about 500° C., preferably from about −40° to about 200° C., and more preferably below about 150° C. to avoid undesirable side reactions. Lower reaction temperatures are preferred to maximize alkylate octane. For example, temperatures as low as −20° C. may be effectively employed. Operating temperature typically falls within the range of about −20° to about 100° C., with the most preferred operating temperatures falling within the range of about −20° to about 40° C.

Operating pressure is generally controlled to maintain the reactants in the liquid phase, and is suitably from about 50 to about 1500 psig, preferably from about 100 to about 500 psig. The catalyst weight hourly space velocity as well as the Lewis acid dosage varies with the particular composite catalyst system employed.

The particular operating conditions used in the present process will depend on the specific alkylation reaction being effected. Process conditions such as temperature, pressure, space velocity and molar ratio of the reactants will affect the characteristics of the resulting alkylate, and may be adjusted within the disclosed range by those skilled in the art with only minimal trial and error.

Water or water-forming materials ma be added to the alkylation reaction zone, for example at a rate which averages from about 0.1 ppmw to about 1 wt. %, based on total hydrocarbon feed rate, preferably at a rate from about 0.1 to about 500 ppmw. The water can be supplied as such or be a feed material which provides water under the alkylation condition selected. Suitable water-forming materials include monohydric and dihydric alcohols which yield water upon undergoing dehydration. Of this group, particular preference is accorded the aliphatic alcohols, especially those containing 1 to 6 carbon atoms, for example, methanol, ethanol, isopropanol, t-butyl alcohol and isopentyl alcohol. The water and/or water-producing material can be added directly to the reactor, that is, as part of the feed and/or it can be incorporated in the catalyst, either by direct contact or by exposing the catalyst to an atmosphere of water and/or water-forming material. The amount of preintroduced water into the catalyst ranges from about 0.5 to about 25 percent by weight of the catalyst, preferably from about 1 to about 10 percent.

Catalysts

The catalyst complex useful in the present invention may comprise a solid as described below promoted by a Lewis acid. A Lewis acid is generally considered to be a molecule which is capable of combining with another molecule or ion by forming covalent chemical bond with two electrons from the second molecule or ion; that is, the Lewis acid is an electron acceptor. Examples of Lewis acids include boron trifluoride ($BF_3$), boron trichloride ($BCl_3$), antimony pentafluoride ($SbF_5$), and aluminum chloride ($AlCl_3$). The present invention contemplates the use of all Lewis acids as those set forth in *Friedel-Crafts and Related Reactions*, Interscience Publishers, Chapters III and IV (1963), which is incorporated herein by reference.

The solid component of the alkylation catalyst comple useful in the present invention comprises an inorganic, porous crystalline phase material having, after calcination, a d-spacing greater than about 18 Angstrom Units and having a benzene adsorption capacity of greater than 15 gram benzene per 100 grams of said material at 50 torr and 25° C.

As demonstrated hereinafter, the inorganic, non-layered mesoporous crystalline material of this invention preferably has the following composition:

$$M_{n/q}(W_a X_b Y_c Z_d O_h)$$

wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1.

A preferred embodiment of the above crystalline material is when (a+b+c) is greater than d, and h =2. A further embodiment is when a and d =0, and h =2.

In the as-synthesized form, the material of this invention has a composition, on an anhydrous basis, expressed empirically as follows:

$$rRM_{n/q}(W_a X_b Y_c Z_d O_h)$$

wherein R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described.

To the extent desired, the original M, e.g. sodium or chloride, ions of the as-synthesized material of this invention can be replaced in accordance with techniques well known in the art, at least in part, by ion exchange with other ions. Preferred replacing ions include metal ions, hydrogen ions, hydrogen precursor, e.g. ammonium, ions and mixtures thereof. Particularly preferred ions are those which tailor the catalytic activity for certain hydrocarbon conversion reactions. These include hydrogen, rare earth metals and metals of Groups IA (e.g. K), IIA (e.g. Ca), VIIA (e.g. Mn), VIIIA (e.g. Ni),IB (e.g. Cu), IIB (e.g. Zn), IIIB (e.g. In), IVB (e.g. Sn), and VIIB (e.g. F) of the Periodic Table of the Elements (Sargent-Welch Scientific Co. Cat. No. S-18806, 1979) and mixtures thereof.

The crystalline (i.e. meant here as having sufficient order to provide a diffraction pattern such as, for example, by X-ray, electron or neutron diffraction, following calcination with at least one peak) mesoporous material of this invention may be characterized by its heretofore unknown structure, including extremely large pore windows, and high sorption capacity. The term "mesoporous" is used here to indicate crystals having uniform pores within the range of from about 13 Angstroms to about 200 Angstroms. The materials of this invention will have uniform pores within the range of from about 13 Angstroms to about 200 Angstroms, more usually from about 15 Angstroms to about 100 Angstroms. For the purposes of this application, a working definition of "porous" is a material that adsorbs at least 1 gram of a small molecule, such as Ar, $N_2$, n-hexane or cyclohexane, per 100 grams of the solid.

Figure 19:
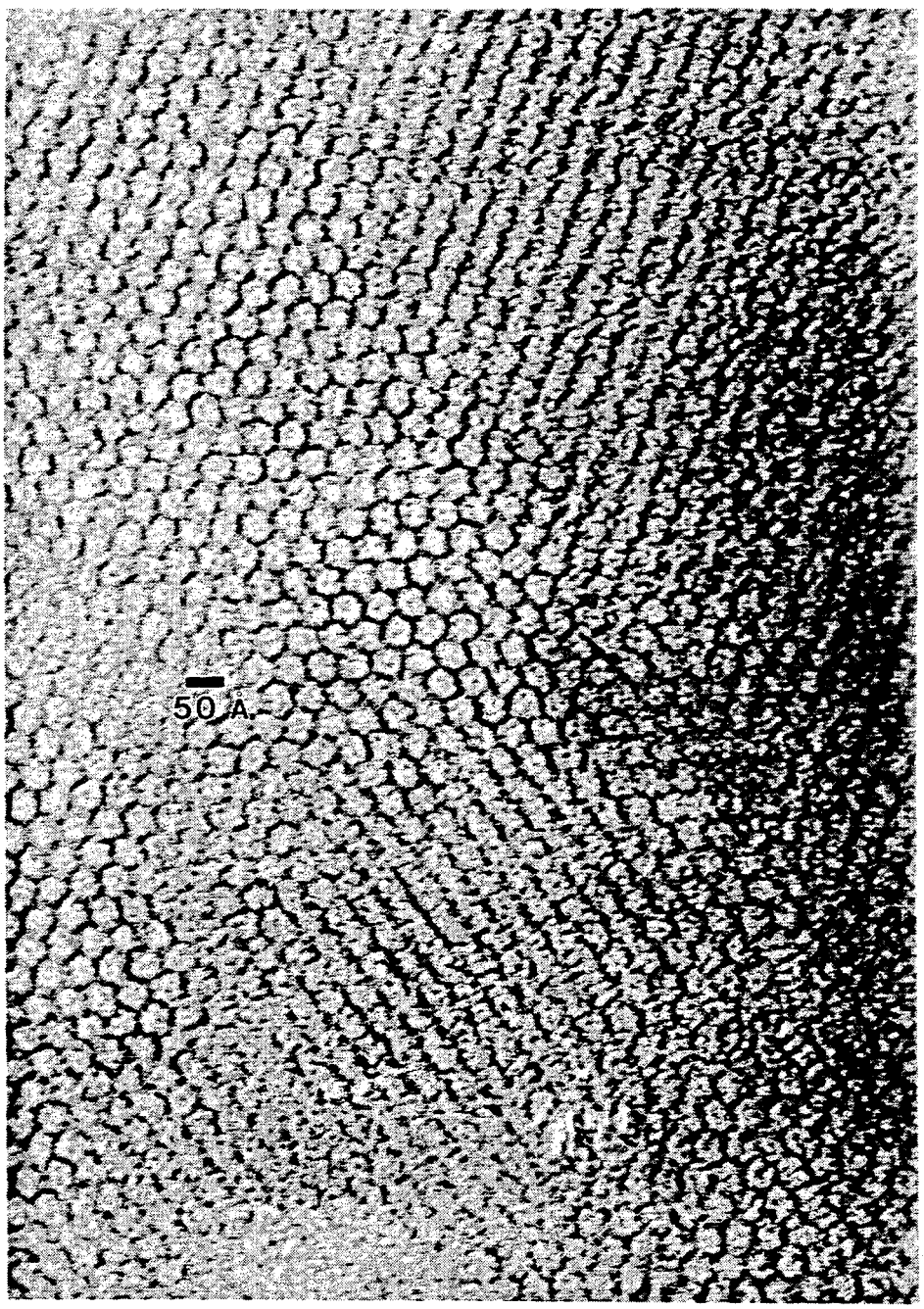
FIG. 19 is a transmission electron micrograph of the product of Example 4.
Figure 20:
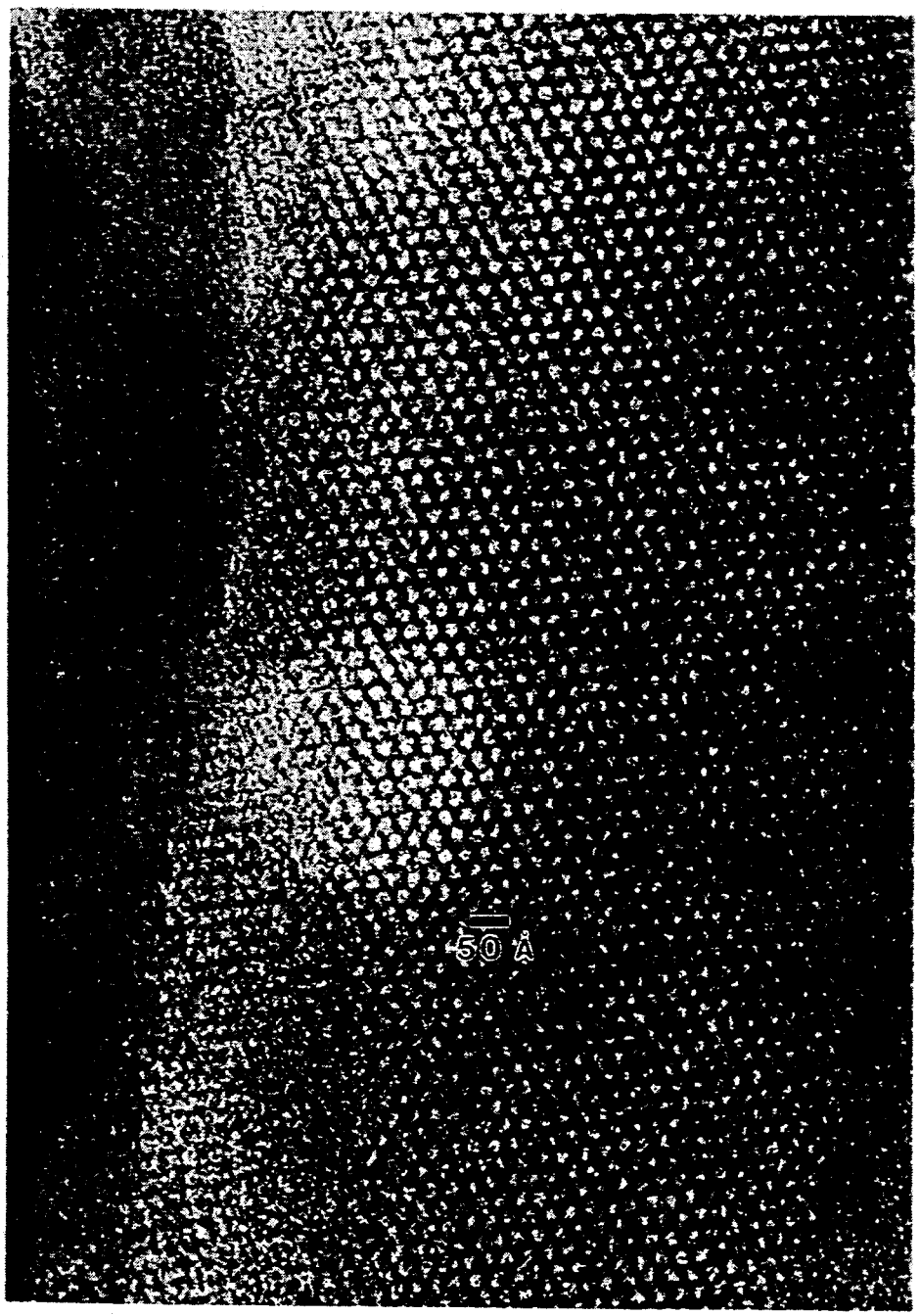
FIG. 20 is a transmission electron micrograph of the product of Example 5.
Figure 21:
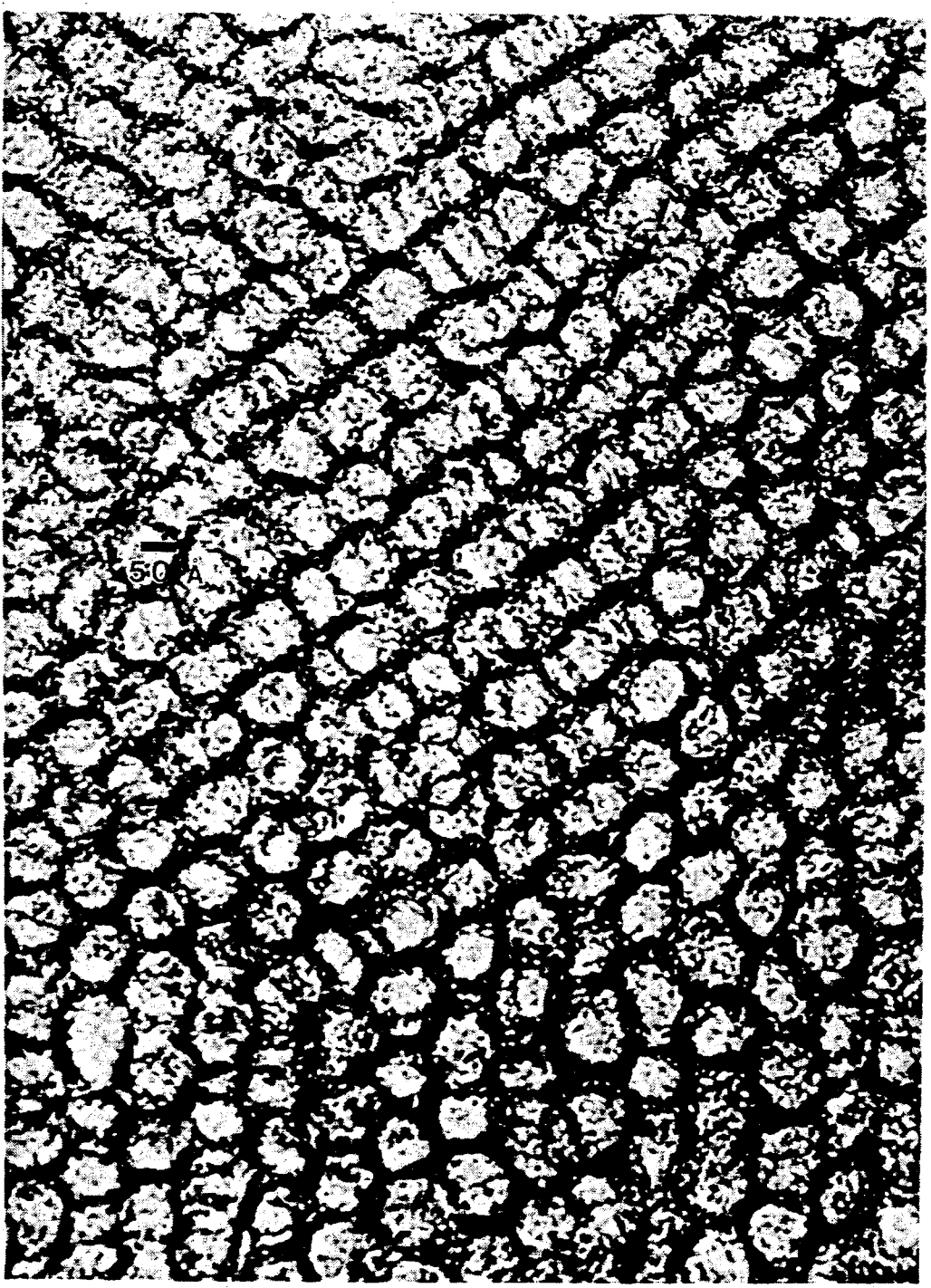
FIG. 21 is a transmission electron micrograph of the product of Example 19.

The material of the present invention can be distinguished from other porous inorganic solids by the regularity of its large open pores, whose pore size more nearly resembles that of amorphous or paracrystalline materials, but whose regular arrangement and uniformity of size (pore size distribution within a single phase of, for example, $\pm 25\%$, usually $\pm 15\%$ or less of the average pore size of that phase) resemble more those of crystalline framework materials such as zeolites. The material appears to have a hexagonal arrangement of large open channels that can be synthesized with open internal diameters from about 13 Angstroms to about 200 Angstroms. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as $\pm 25\%$ random deviation from the average repeat distance between adjacent channels still clearly give recognizable images of the present ultra-large pore materials. Comparable variations are also observed in the $d_{100}$ values from the electron diffraction patterns. Transmission electron micrographs of materials within this working definition are shown in FIGS. 19, 20, and 21.

The most regular preparations of the material of the present invention give an X-ray diffraction pattern with a few distinct maxima in the extreme low angle region. The positions of these peaks approximately fit the positions of the hkO reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hkO projection of the hexagonal lattice and is related to the repeat distance a between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hkO subset of unique reflections of 100, 110, 200, 210, etc., and their symmetry-related reflections.

In its calcined form, the crystalline material of the invention may be further characterized by an X-ray diffraction pattern with at least one peak at a position greater than about 18 Angstrom Units d-spacing (4.909 degrees two-theta for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, and organics may be removed by contact with acid or base or other chemical agents such that the detrital material will be removed without detrimental effect on the crystal of the invention.

More particularly, the calcined crystalline non-layered material of the invention may be characterized by an X-ray diffraction patter with at least two peaks at positions reater than about 10 Angstrom Units d-spacing (8.842 degrees two-theta for Cu K-alpha radiation), at least one of which is at a position greater than about 18 Angstrom Units d-spacing, and no peaks at positions less than about 10 Angstrom units d-spacing with relative intensity greater than about 20% of the strongest peak. Still more particularly, the X-ray diffraction pattern of the calcined material of this invention will have n peaks at positions less than about 10 Angstrom units d-spacing with relative intensity greater than about 10% of the strongest peak. In any event, at least one peak in the X-ray diffraction pattern will have a d-spacing that corresponds to the $d_{100}$ value of the electron diffraction pattern of the material. Still more particularly, the calcined inorganic, non-layered crystalline material of the invention is characterized as having a pore size of about 13 Angstroms or greater as measured by physisorption measurements, hereinafter more particularly set forth. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Angstrom units (A), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75–100), s=strong (50–74), m=medium (25–49) and w=weak (0–24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

When used as a sorbent or catalyst component, the composition of the invention should be subjected to treatment to remove part or all of any organic constituent. The present composition can also be used as a catalyst component in intimate combination with a hydrogenating component such as tungsten, vanadium, molybdenum, rhenium, nickel, cobalt, chromium, manganese, or a noble metal such as platinum or palladium or mixtures thereof where a hydrogenation-dehydrogenation function is to be performed. Such component can be in the composition by way of co-crystallization, exchanged into the composition to the extent a Group IIIB element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platitnous chloride and various compounds containing the platinum amine complex.

The above crystalline material, especially in its metal, hydrogen and ammonium forms can be beneficially converted to another form by thermal treatment (calcination). This thermal treatmeht is generally performed by heating one of these forms at a temperature of at least 400° C. for at least 1 minute and generally not longer than 20 hours, preferably from about 1 to about 10 hours. While subatmospheric pressure can be employed for the thermal treatment, atmospheric pressure is desired for reasons of convenience, such as in air, nitrogen, ammonia, etc. The thermal treatment can be performed at a temperature up to about 750° C. The thermally treated product is particularly useful in the catalysis of certain hydrocarbon conversion reactions.

The crystalline material of this invention, when employed either as an adsorbent or as a catalyst component in an organic compound conversion process should be dehydrated, at least partially. This can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The present crystalline material can be prepared by one of several methods, each with particular limitations.

A first method involves a reaction mixture having an $X_2O_3/YO_2$ mole ratio of from 0 to about 0.5, but an $Al_2O_3/SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, hereinafter more particularly described. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, hereinafter more particularly described, and a solvent or solvent mixture, such as, for example, $C_1$–$C_6$ alcohols, $C_1$–$C_6$ diols and/or water, especially water, said reaction mixture having a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $Al_2O_3/SiO_2$ | 0 to 0.01 | 0.001 to 0.01 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/ $(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/$ | 0.01 to 2.0 | 0.03 to 1.0 |

| Reactants | Useful | Preferred |
|---|---|---|
| $(YO_2 + WO + Z_2O_5 + X_2O_3)$ | | | wherein e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O/(YO_2+WO+Z_2O_5+X_2O_3)$ ratio is important. When this ratio is less than 0.01 or greater than 2.0, impurity products tend to be synthesized at the expense of the present material.

A second method for synthesis of the present crystalline material involves a reaction mixture having an $X_2O_3/YO_2$ mole ratio of from about 0 to about 0.5, a crystallization temperature of from about 25° C. to about 250° C., preferably from about 50° C. to about 175° C., and two separate organic directing agents, i.e. the organic and additional organic directing agents, hereinafter more particularly described. This second method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, a combination of organic directing agent and additional organic directing agent (R), each hereinafter more particularly described, and a solvent or solvent mixture, such as, for example, $C_1$-$C_6$ alcohols, $C_1$-$C_6$ diols and/or water, especially water, said reaction mixture having a composition, in terms of mole ratios of oxides, within the following ranges:

| Reactants | Useful | Preferred |
|---|---|---|
| $X_2O_3/YO_2$ | 0 to 0.5 | 0.001 to 0.5 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/$(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.1 to 2.0 | 0.12 to 1.0 | wherein e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the pH is not narrowly important for crystallization of the present invention.

A third method for synthesis of the present crystalline material is where X comprises aluminum and Y comprises silicon, the crystallization temperature must be from about 25° C. to about 175° C., preferably from about 50° C. to about 150° C., and an organic directing agent, hereinafter more particularly described, or, preferably a combination of that organic directing agent plus an additional organic agent, hereinafter more particularly described, is used. This third method comprises preparing a reaction mixture containing sources of, for example, alkali or alkaline earth metal (M), e.g. sodium or potassium, cation if desired, one or more sources of aluminum and/or silicon, an organic (R) directing agent, hereinafter more particularly described, and a solvent or solvent mixture, such as, for example $C_1$-$C_6$ alcohols, $C_1$-$C_6$ diols and/or water, especially water, said reaction mixture having a composition, in terms of mole ratios of oxides, within the following ranges:

| Reactants | Useful | Preferred |
|---|---|---|
| $Al_2O_3/SiO_2$ | 0 to 0.5 | 0.001 to 0.5 |
| Solvent/$SiO_2$ | 1 to 1500 | 5 to 1000 |
| $OH^-/SiO_2$ | 0 to 10 | 0 to 5 |
| $(M_{2/e}O + R_{2/f}O)/(SiO_2 + Al_2O_3)$ | 0.01 to 20 | 0.05 to 5 |
| $M_{2/e}O/(SiO_2 + Al_2O_3)$ | 0 to 5 | 0 to 3 |
| $R_{2/f}O/(SiO_2 + Al_2O_3)$ | 0.01 to 2 | 0.03 to 1 | wherein e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add the sources of oxides, e.g. silica and/or alumina such that the ratio of $R_{2/f}O/(SiO_2Al_2O_3)$ is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the present synthesis involves th reaction mixture used for the third method, but the following specific procedure with tetraethylorthosilicate the source of silicon oxide:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_{2/f}O/SiO_2$ mole ratio is in the range of from about 0.5 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

In each of the above methods, batch crystallization of the present crystalline material can be carried out under either static or agitated, e.g. stirred, conditions in a suitable reactor vessel, such as for example, polypropylene jars or teflon lined or stainless steel autoclaves. Crystallization may also be conducted continuously in suitable equipment. The total useful rang of temperatures for crystallization is noted above for each method for a time sufficient for crystallization to occur at the temperature used, e.g. from about 5 minutes to about 14 days. Thereafter, the crystals are separated from the liquid and recovered.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

By adjusting conditions of the synthesis reaction for each method, like temperature, pH and time of reaction, etc., within the above limits, embodiments of the present non-layered crystalline material with a desired average pore size may be prepared. In particular, changing the pH, the temperature or the reaction time may promote formation of product crystals with different average pore size. Non-limiting examples of various combinations of W, X, Y and Z contemplated for the first and second synthesis methods of the present invention include:

| W | X | Y | Z |
| --- | --- | --- | --- |
| — | Al | Si | — |
| — | Al | — | P |
| — | Al | Si | P |
| Co | Al | — | P |
| Co | Al | Si | P |
| — | — | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula $R_1R_2R_3R_4Q^+$, i.e.:

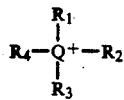

wherein Q is nitrogen or phosphorus and wherein at least one of $R_1$, $R_2$, $R_3$ and $R_4$ is aryl or alkyl of from 6 to about 36 carbon atoms, e.g. $-C_6H_{13}$, $-C_{10}H_{21}$, $-C_{16}H_{33}$ and $-C_{18}H_{37}$, or combinations thereof, the remainder of $R_1$, $R_2$, $R_3$ and $R_4$ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula wherein $R_1$, $R_2$, $R_3$ and $R_4$ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the presently required directing agent, when compared with other such agents known to direct synthesis of one or more other crystal structures, is believed due to its ability to function as template in the above reaction mixture in the nucleation and growth of the desired ultra-large pore crystals with the limitations discussed above. Non-limiting examples of these directing agents include cetyltrimethylammonium, cetyltrimethylphosphonium, octadecyltrimethylphosphonium, benzyltrimethylammonium, cetylpyridinium, myristyltrimethylammonium, decyltrimethylammonium, dodecyltrimethylammonium and dimethyldidodecylammonium.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

As in the case of many catalysts, it may be desired to incorporate the new crystal composition with another material resistant to the temperatures and other conditions employed in organic conversion processes. Such materials include active and inactive materials and synthetic or naturally occurring zeolites as well as inorganic materials such as clays, silica and/or metal oxides such as alumina, titania and/or zirconia. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated with naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

It may be desirable to provide at least a part of the foregoing matrix materials in colloidal form so as to facilitate extrusion of the bound catalyst components(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane, benzene and/or n-hexane, they are Equilibrium Adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C. The present composition exhibits an equilibrium benzene adsorption capacity at 50 Torr and 25 C of greater than about 15 grams/100 grams, particularly greater than about 17.5 g/100 g/ and more particularly greater than about 20 g/100 g.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures. Sorption is complete when the pressure change is not sufficient to activate the manostat.

Another way of doing this for benzene adsorption data is on a suitable thermogravimetric analysis system, such as a computer-controlled 990/951 duPont TGA system. The adsorbent sample is dehydrated (physically sorbed water removed) by heating at, for example, about 350° C. or 500° C. to constant weight in flowing helium. If the sample is in as-synthesized form, e.g. containing organic directing agents, it is calcined at about 540° C. in air and held to constant weight instead of the previously described 350° C. or 500° C. treatment. Benzene adsorption isotherms ar measured at 25° C. by blending a benzene saturated helium gas stream with a pure helium gas stream in the proper proportions to obtain the desired benzene partial pressure. The value of the adsorption at 50 Torr of benzene is taken from a plot of the adsorption isotherm.

In the examples, percentages are by weight unless otherwise indicated.

EXAMPLE 1

One hundred grams of cetyltrimethylammonium (CTMA) hydroxide solution, prepared by contacting a 29 wt. % N,N,N-trimethyl-1-hexadecanaminium chloride solution with a hydroxide-for-halide exchange resin, was combined with 100 grams of an aqueous solution of tetramethylammonium (TMA) silicate (10% silica) with stirring. Twenty-five grams of HiSil, a precipitated hydrated silica containing about 6 wt.% free water and about 4.5 wt.% bound water of hydration and having an ultimate particle size of about 0.02 micron, was added. The resulting mixture was placed in a polypropylene bottle, which was kept in a steam box at 95° C. overnight. The mixture had a composition in terms of moles per mole $Al_2O_3$:

2.7 moles $Na_2O$
392 moles $SiO_2$
35.7 moles $(CTMA)_2O$
61.7 moles $(TMA)_2O$
6231 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 475 m$^2$/g and the following equilibrium adsorption capacities in grams/100 grams:

| | |
|---|---|
| $H_2O$ | 8.3 |
| Cyclohexane | 22.9 |
| n-Hexane | 18.2 |
| Benzene | 21.5 |

The X-ray diffraction pattern of the calcined product of this example is shown in FIG. 1. In this and the following Figures, it is noted that 10 Angstrom Units d-spacing corresponds to 8.842 degrees 2-theta (Cu K-alpha radiation) and 18 Angstrom Units corresponds to 4.909 degrees.

The product of this example may be characterized as including a very strong relative intensity line at 37.8±2.0 Angstroms d-spacing, and weak lines at 21.6±1.0 and 19.2±1.0 Angstroms. The present ultra-large pore material was demonstrated to be in the product of this example by transmission electron microscopy (TEM), which produced images of a hexagonal arrangement of uniform pores and hexagonal electron diffraction pattern with a $d_{100}$ value of about 39 Angstroms.

EXAMPLE 2

One hundred grams of cetyltrimethylammonium (CTMA) hydroxide solution prepared as in Example 1 was combined with 100 grams of an aqueous solution of tetramethylammonium (TMA) hydroxide (25%) with stirring. Twenty-five grams of HiSil, a precipitated hydrated silica containing about 6 wt.% free water and about 4.5 wt.% bound water of hydration and having an ultimate particle size of about 0.02 micron, was added. The resulting mixture was placed in a static autoclave at 150° C. overnight. The mixture had a composition in terms of moles per mole $Al_2O_3$:

2.7 moles $Na_2O$
291 moles $SiO_2$
35.7 moles $(CTMA)_2O$
102 moles $(TMA)_2O$
6120 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 993 m²/g and the following equilibrium adsorption capacities in grams/100 grams:

| | |
|---|---|
| $H_2O$ | 7.1 |
| Cyclohexane | 47.2 |
| n-Hexane | 36.2 |
| Benzene | 49.5 |

Figure 2:
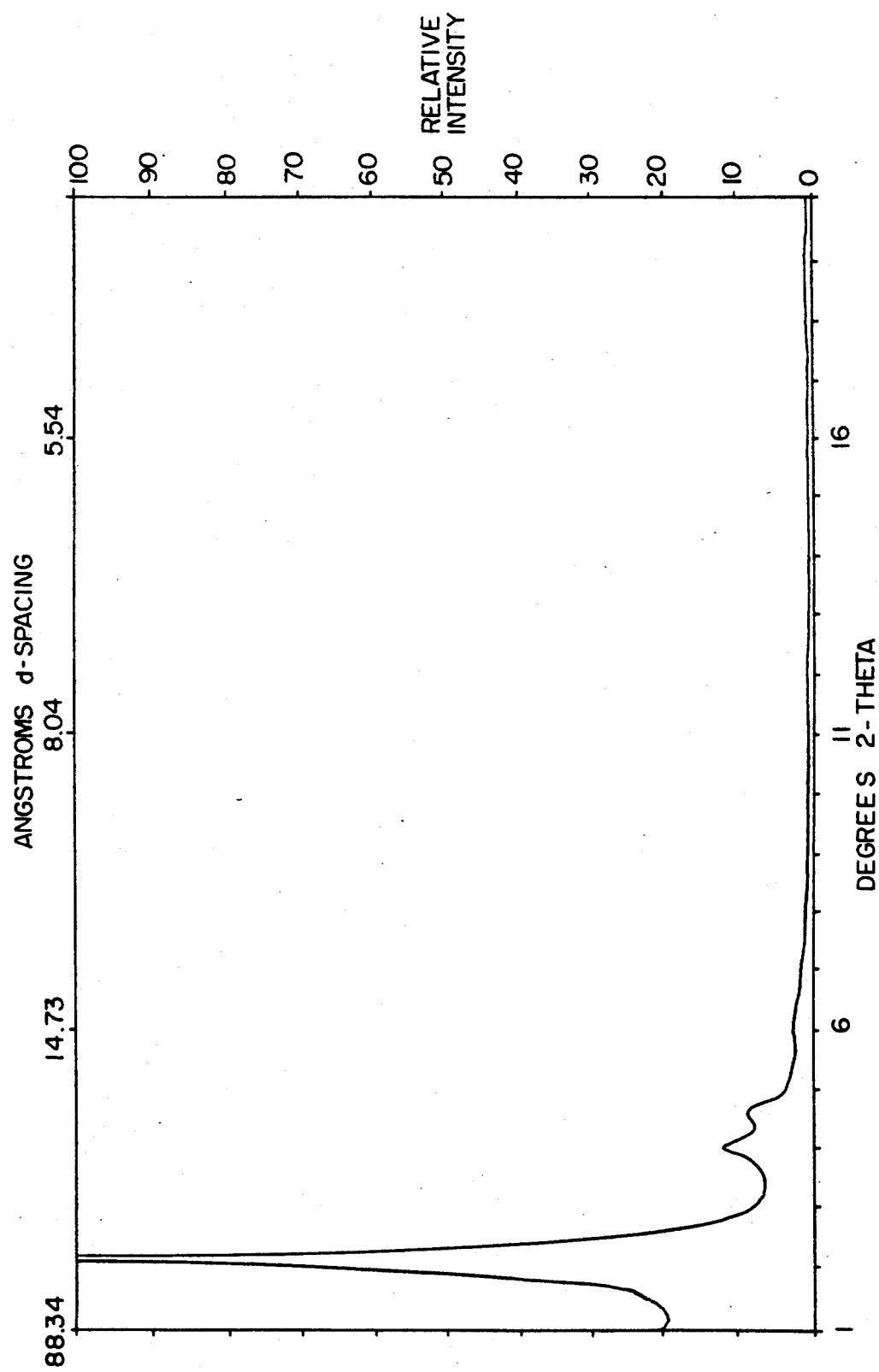

The X-ray diffraction pattern of the calcined product of this example is shown in FIG. 2. It may be characterized as including a very strong relative intensity line at 39.3±2.0 Angstroms d-spacing, and weak lines at 22.2±1.0 and 19.4±1.0 Angstroms. TEM indicated that the product contained the present ultra-large por material.

A portion of the above product was then contacted with 100% steam at 1450° F. for two hours. The surface area of the steamed material was measured to be 440 m²/g, indicating that about 45% was retained following severe steaming.

Another portion of the calcined product of this example was contacted with 100% steam at 1250° F. for two hours. The surface area of this material was measured to be 718 m²/g, indicating that 72% was retained after steaming at these conditions.

EXAMPLE 3

Water, cetyltrimethylammonium hydroxide solution prepared as in Example 1, aluminum sulfate, HiSil and an aqueous solution of tetrapropylammonium (TPA) bromide (35%) were combined to produce a mixture having a composition in terms of moles per mole $Al_2O_3$:

0 65 moles $Na_2O$
65 moles $SiO_2$
8.8 moles $(CTMA)_2O$
1336 moles $H_2O$

The resulting mixture was placed in a polypropylene bottle, which was kept in steam box at 95° C. for 192 hours. The sample was then cooled to room temperature and combined with CTMA hydroxide solution prepared as in Example 1 and TMA hydroxide (25% by weight) in the weight ratio of 3 parts mixture, 1 part CTMA hydroxide and 2 parts TMA hydroxide. The combined mixture was then placed in a polypropylene bottle and kept in a steam box at 95° C. overnight. The combined mixture had a composition in terms of moles per mole $Al_2O_3$:

0.65 moles $Na_2O$
65 moles $SiO_2$
15 moles $(CTMA)_2O$
1.22 moles $(TPA)_2O$
35.6 moles $(TMA)_2O$
2927 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 1085 m²/g and the following equilibrium adsorption capacities in grams/100 grams:

| | |
|---|---|
| $H_2O$ | 11.5 |
| Cyclohexane | >50 |
| n-Hexane | 39.8 |
| Benzene | 62 |

Figure 3:
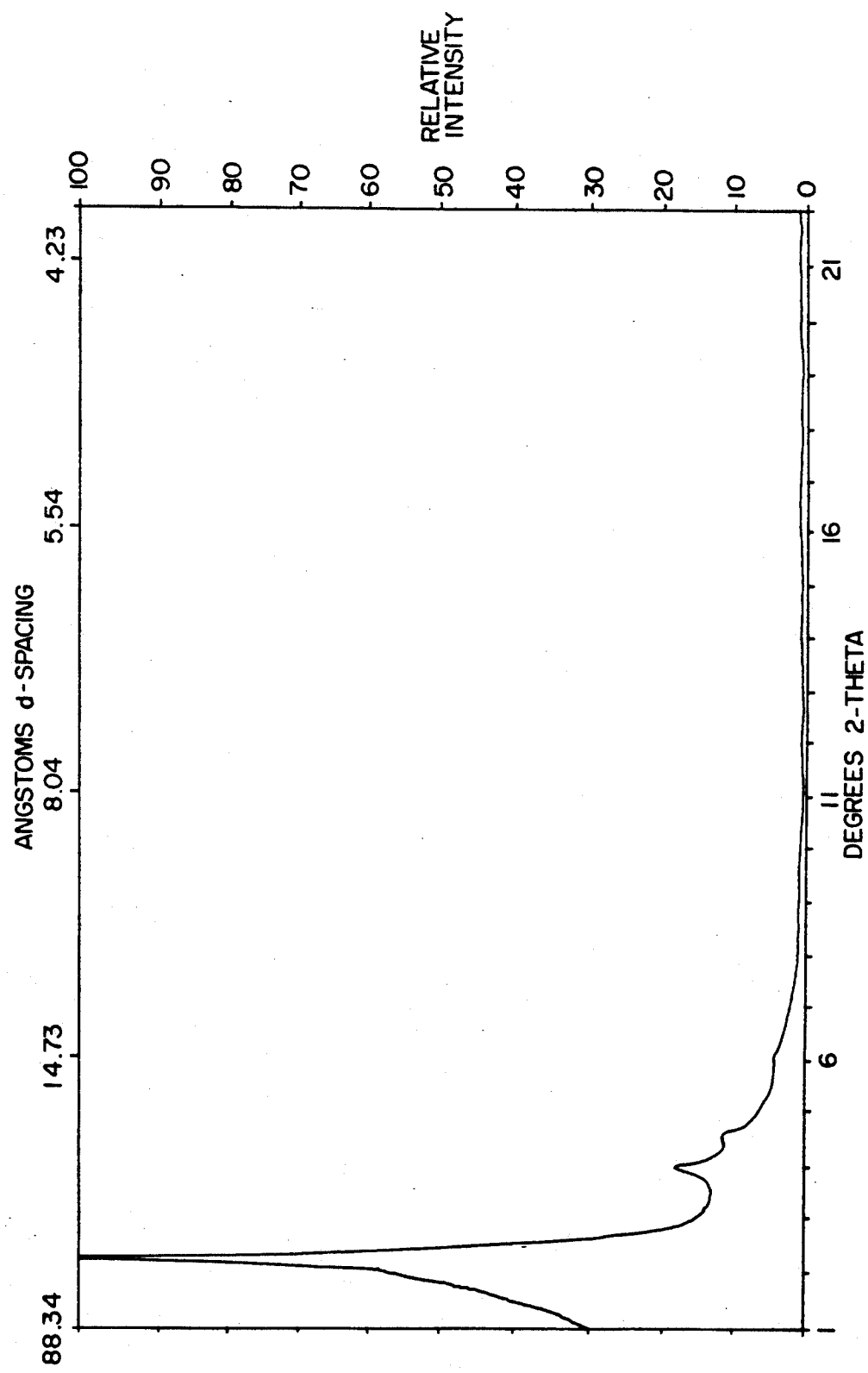

The X-ray diffraction pattern of the calcined product of this example is shown in FIG. 3. The product of this example may be characterized as including a very strong relative intensity line at 38.2±2.0 Angstroms d-spacing, and weak lines at 22.2±1.0 and 19.4±1.0 Angstroms. TEM indicated the product contained the present ultra-large pore material.

EXAMPLE 4

Two hundred grams of cetyltrimethylammonium (CTMA) hydroxide solution prepared as in Example 1 was combined with 2 grams of Catapal alumina (alpha-alumina monohydrate, 74% alumina) and 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 48 hours. The mixture had a composition in terms of moles per mole $Al_2O_3$:

0.23 moles $Na_2O$
33.2 moles $SiO_2$
6.1 moles $(CTMA)_2O$
5.2 moles $(TMA)_2O$
780 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 1,043 m²/g and the following equilibrium adsorption capacities in grams/100 grams:

| | |
|---|---|
| $H_2O$ | 6.3 |
| Cyclohexane | >50 |
| n-Hexane | 49.1 |
| Benzene | 66.7 |

Figure 4:
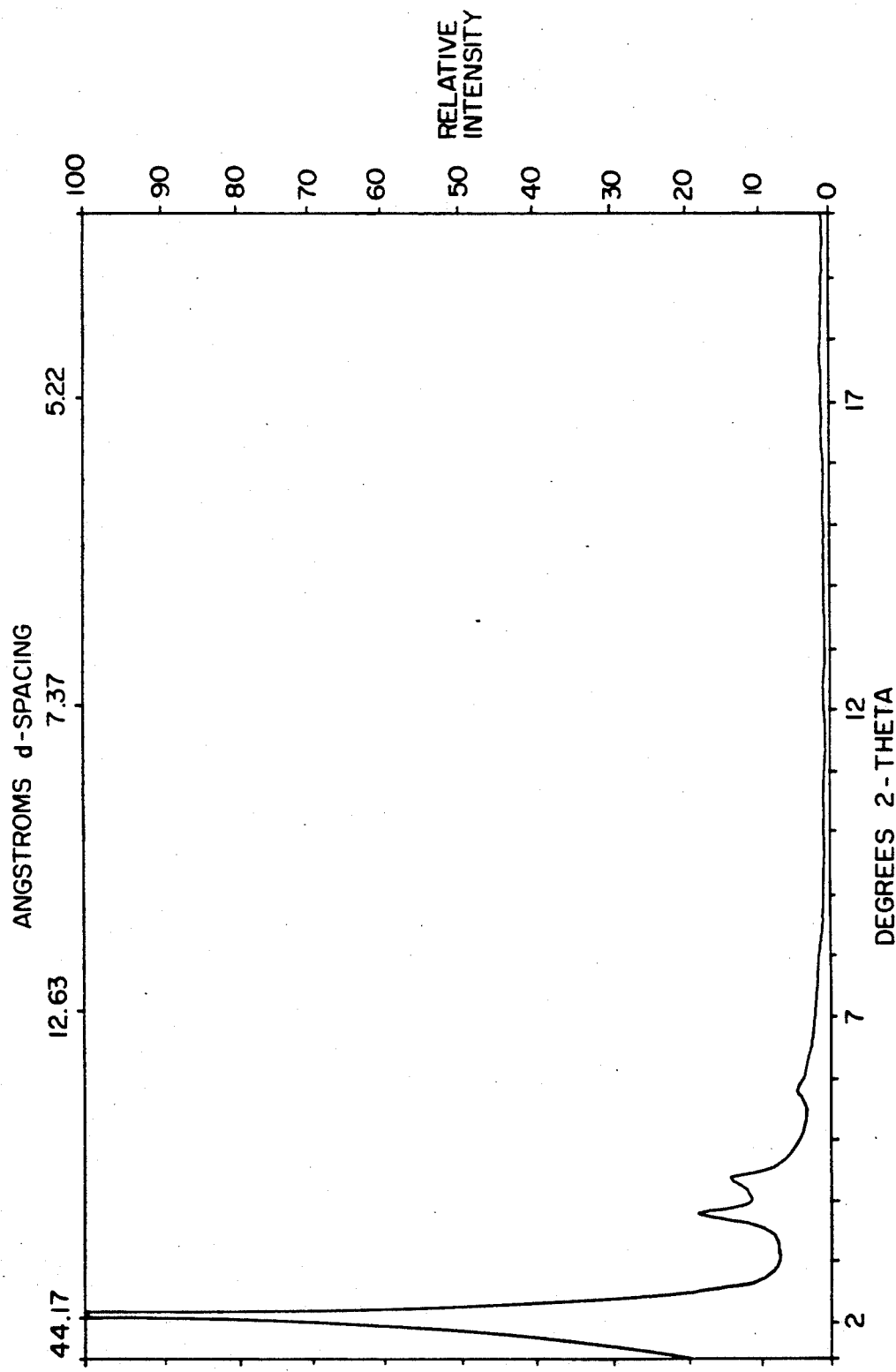

The X-ray diffraction pattern of the calcined product of this example is shown in FIG. 4. It may be characterized as including a very strong relative intensity line at 40.8±2.0 Angstroms d-spacing, and weak lines at 23.1±1.0 and 20.1±1.0 Angstroms. TEM indicated that the product contained the present ultra-large pore material (see Example 23).

EXAMPLE 5

Two-hundred sixty grams of water was combined with 77 grams of phosphoric acid (85%), 46 grams of Catapal alumina (74% alumina), and 24 grams of pyrrolidine (Pyr) with stirring. This first mixture was placed in a stirred autoclave and heated to 150° C. for six days. The material was filtered, washed and air-dried. Fifty grams of this product was slurried with 200 grams of water and 200 grams of cetyltrimethylammonium hydroxide solution prepared as in Example 1. Four hundred grams of an aqueous solution of tetraethylammonium silicate (10% silica) was then added to form a second mixture which was placed in a polypropylene bottle and kept in a steam box at 95° C. overnight. The first mixture had a composition in terms of moles per mole $Al_2O_3$:

1.0 moles $P_2O_5$
0.51 moles $(Pyr)_2O$
47.2 moles $H_2O$

The resulting solid product was recovered by filtration and dried in air at ambient temperature. The product was then calcined at 540° C. for 1 hour in nitrogen, followed by 6 hours in air.

The calcined product proved to have a surface area of 707 $m^2/g$ and the following equilibrium adsorption capacities in grams/100 grams:

| | |
|---|---|
| $H_2O$ | 33.2 |
| Cyclohexane | 19.7 |
| n-Hexane | 20.1 |
| Benzene | 23.3 |

Figure 5:
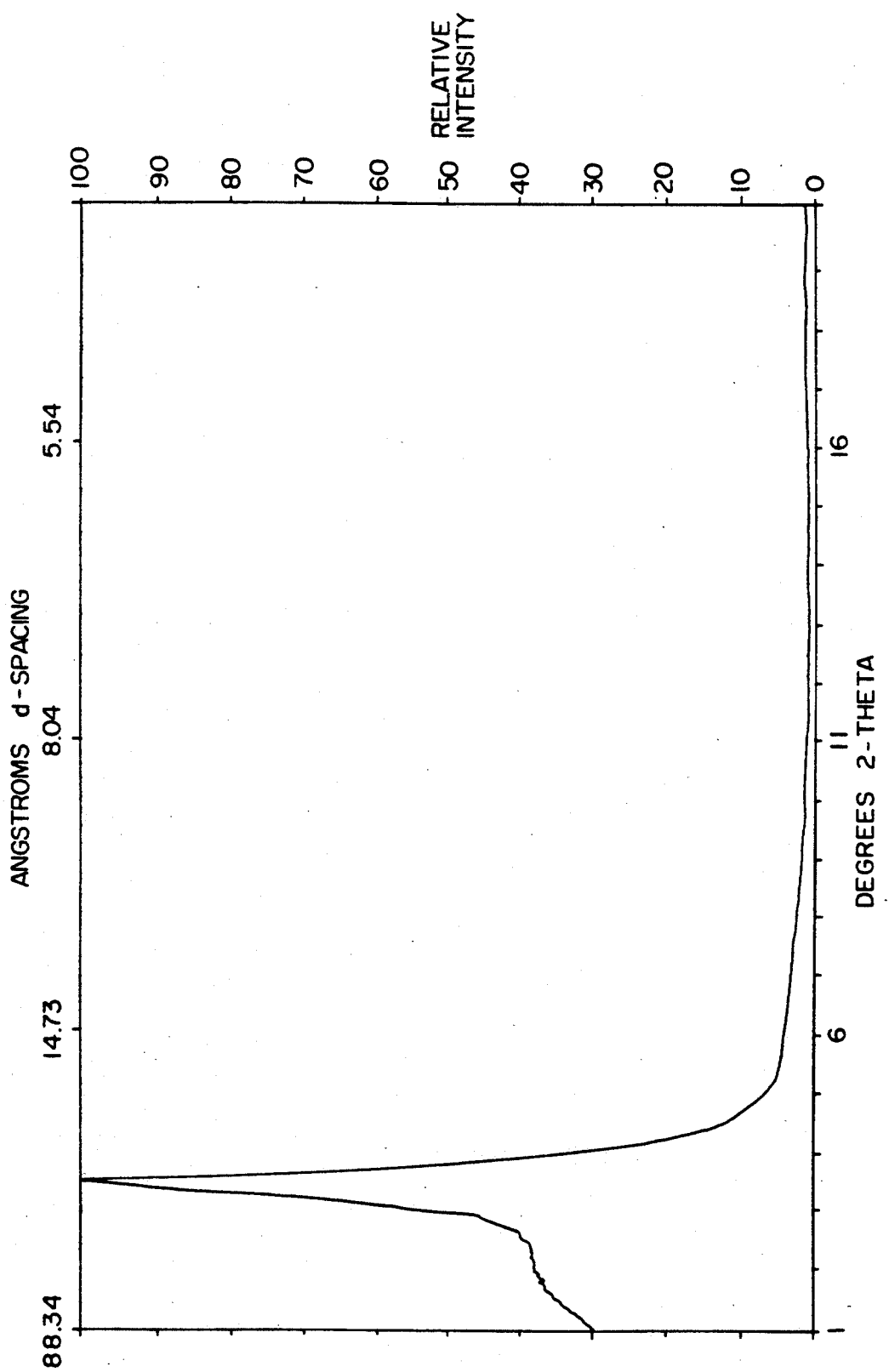

The X-ray diffraction pattern of the calcined product of this example is shown in FIG. 5. It may be characterized as including a very strong relative intensity line at 25.4±1.5 Angstroms d-spacing. TEM indicated the product contained the present ultra-large pore material (see Example 23).

EXAMPLE 6

A solution of 1.35 grams of $NaAlO_2$ (43.5% $Al_2O_3$, 30% $Na_2O$) dissolved in 45.2 grams of water was mixed with 17.3 grams of NaOH, 125.3 grams of colloidal silica (40%, Ludox HS-40) and 42.6 grams of 40% aqueous solution of tetraethylammonium (TEA) hydroxide. After stirring overnight, the mixture was heated for 7 days in a steam box (95° C.). Following filtration, 151 grams of this solution was mixed with 31 grams of cetyltrimethylammonium hydroxide solution prepared as in Example 1 and stored in the steam box at 95° C. for 13 days. The mixture had the following relative molar composition:

0.25 moles $Al_2O_3$
10 moles $Na_2O$
36 moles $SiO_2$
0.95 moles $(CTMA)_2O$
2.5 moles $(TEA)_2O$
445 moles $H_2O$ The resulting solid product was recovered by filtration and washed with water and ethanol. The product was then calcined at 540° C. for 1 hour in nitrogen, followed by 6 hours in air.

The calcined product composition included 0.14 wt. % Na, 68.5 wt. % $SiO_2$ and 5.1 wt. % $Al_2O_3$, and proved to have a benzene equilibrium adsorption capacity of 58.6 grams/100 grams.

Figure 6:
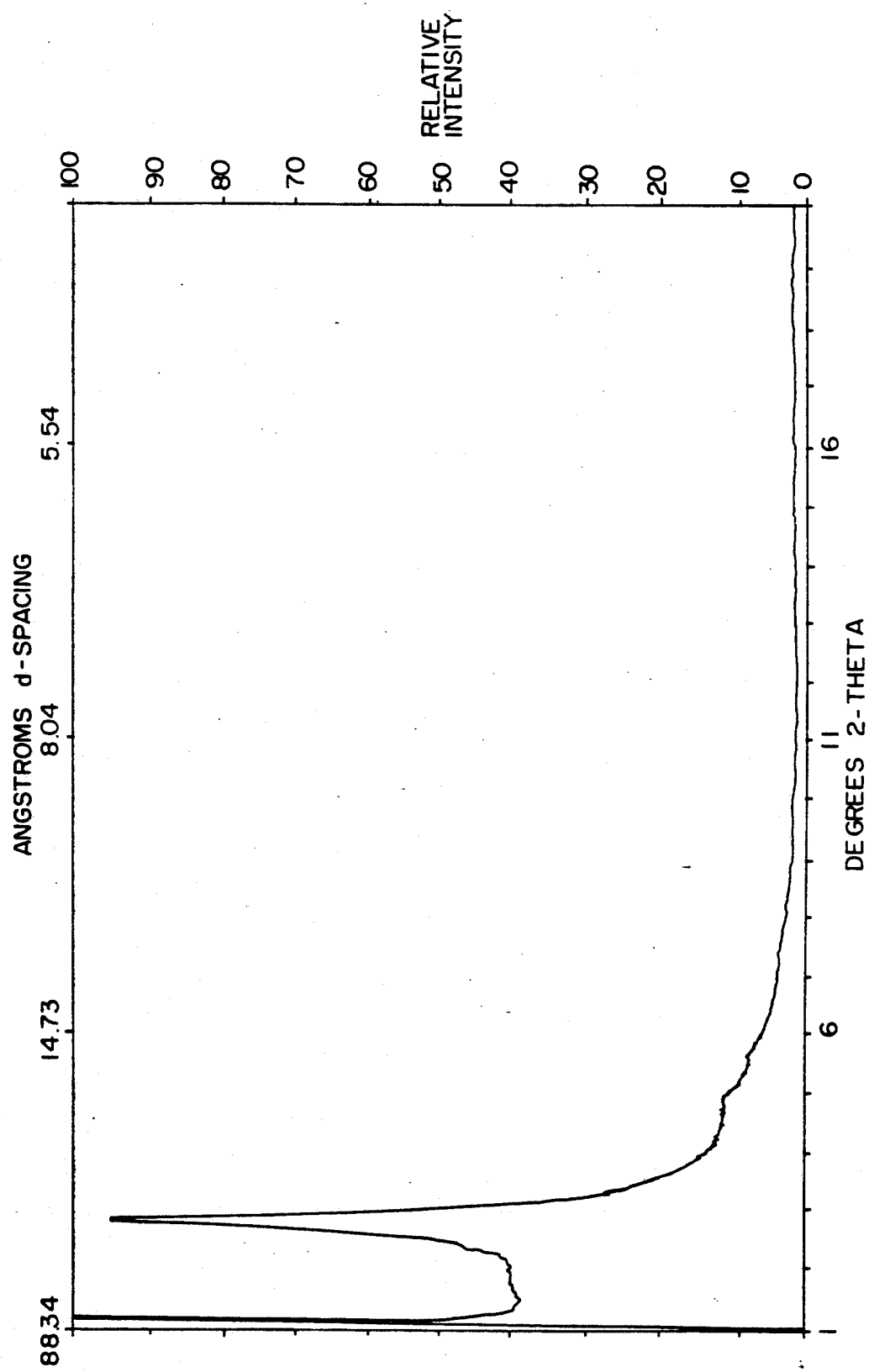

The X-ray diffraction pattern of the calcined product of this example is shown in FIG. 6. The product of this example may be characterized as including a very strong relative intensity line at 31.4±1.5 Angstroms d-spacing. TEM indicated that the product contained the present ultra-large pore material.

EXAMPLE 7

A mixture of 300 gram of cetyltrimethylammonium (CTMA) hydroxide solution prepared as in Example 1 and 41 grams of colloidal silica (40%, Ludox HS-40) was heated in a 600 cc autoclave at 150° C. for 48 hours with stirring at 200 rpm. The mixture has a composition in terms of moles per mole $SiO_2$:

0.5 mole $(CTMA)_2O$
46.5 moles $H_2O$

The resulting solid product was recovered by filtration, washed with water, then calcined at 540° C. for 1 hour in nitrogen, followed by 10 hours in air.

The calcined product composition included less than 0.01 wt. % Na, about 98.7 wt. % $SiO_2$ and about 0.01 wt. % $Al_2O_3$, and proved to have a surface area of 896 $m^2/g$. The calcined product had the following equilibrium adsorption capacities in grams/100 grams:

| | |
|---|---|
| $H_2O$ | 8.4 |
| Cyclohexane | 49.8 |
| n-Hexane | 42.3 |
| Benzene | 55.7 |

Figure 7:
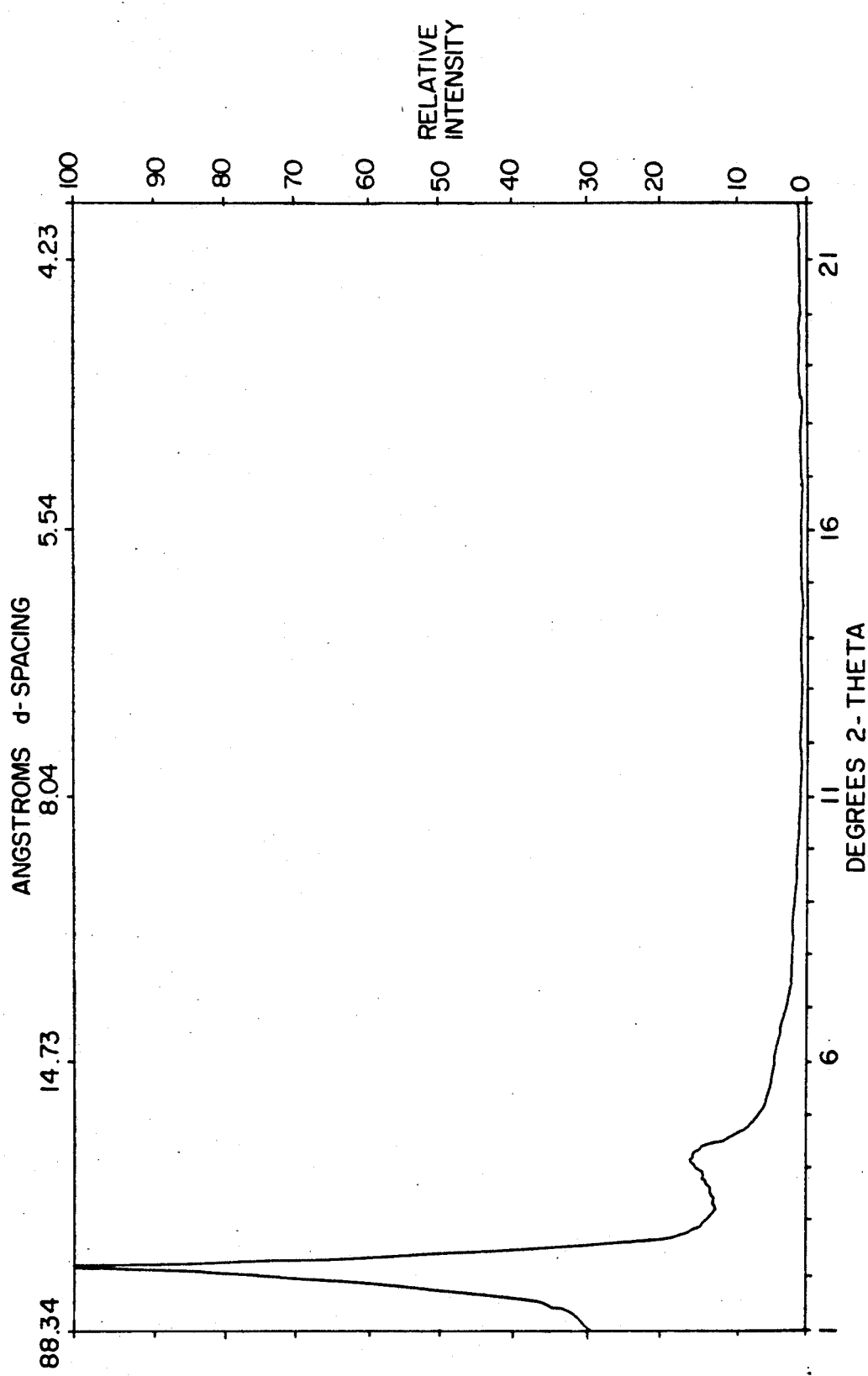

The X-ray diffraction pattern of the calcined product of this example is shown in FIG. 7. It may be characterized as including a very strong relative intensity line at 40.0±2.0 Angstroms d-spacing and a weak line at 21.2±1.0 Angstroms. TEM indicated that the product of this example contained at least three separate phases, one of which was the present ultra-large pore material.

EXAMPLE 8

A mixture of 150 grams of cetyltrimethylammonium (CTMA) hydroxide solution prepared as in Example 1 and 21 grams of colloidal silica (40%, Ludox HS-40) with an initial pH of 12.64 was heated in a 300 cc autoclave at 150° C. for 48 hours with stirring at 200 rpm. The mixture had a composition in terms of moles per mole $SiO_2$:

0.5 mole $(CTMA)_2O$
46.5 moles $H_2O$

The resulting solid product was recovered by filtration, washed with water, then calcined at 540° C. for 6 hours in air.

The calcined product composition was measured to include 0.01 wt. % Na, 93.2 wt. % $SiO_2$ and 0.016 wt. % $Al_2O_3$, and proved to have a surface area of 992 $m^2/g$ and the following equilibrium adsorption capacities in grams/100 grams:

| | |
|---|---|
| $H_2O$ | 4.6 |
| Cyclohexane | >50 |
| n-Hexane | >50 |
| Benzene | 62.7 |

Figure 8:
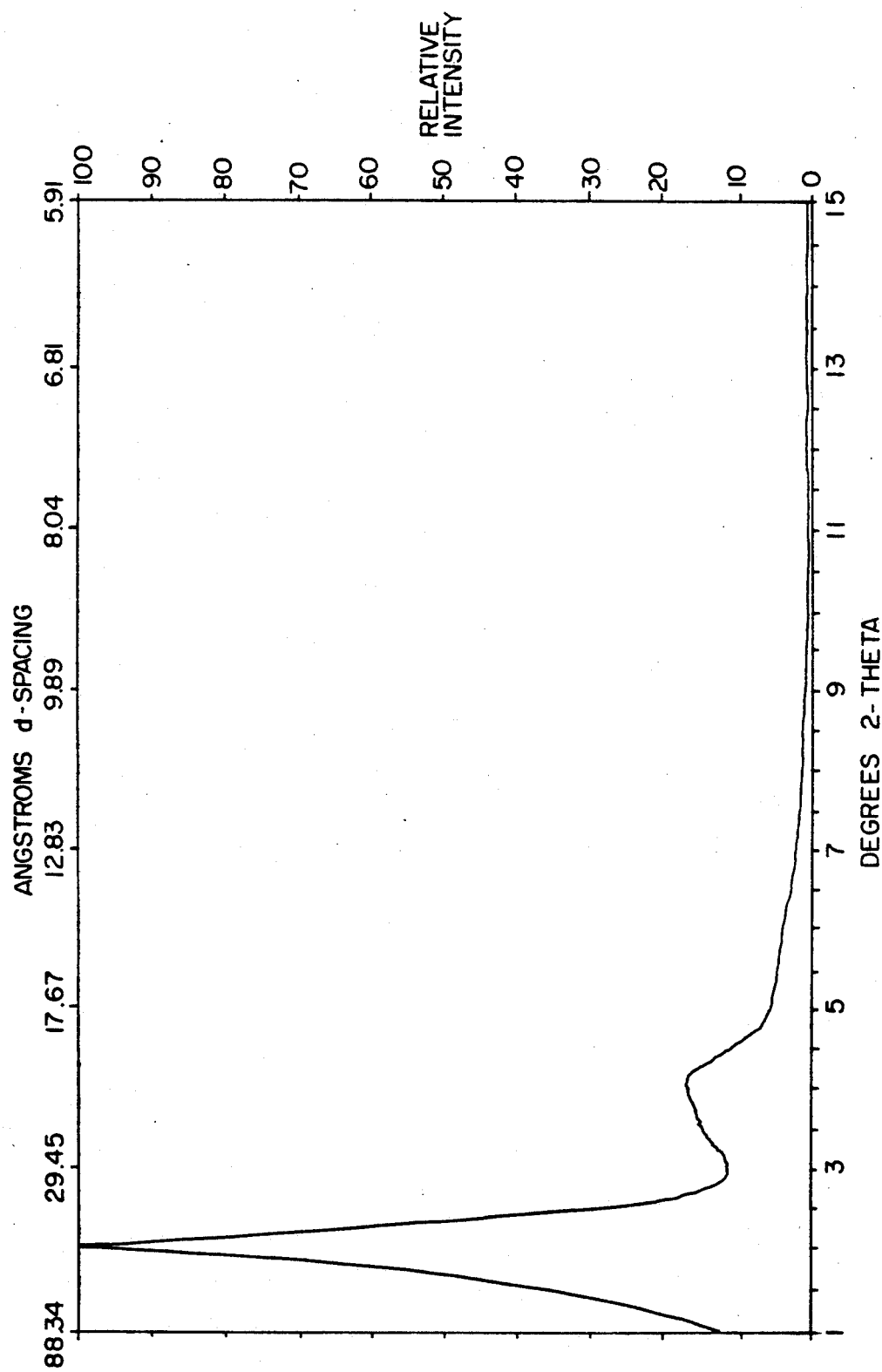

The X-ray diffraction pattern of the calcined product of this example is shown in FIG. 8. This product may be characterized as including a very strong relative intensity line at 43.6±2.0 Angstroms d-spacing and weak lines at 25.1±1.5 and 21.7±1.0 Angstroms. TEM indicated that the product contained the present ultra-large pore material.

EXAMPLE 9

Sodium aluminate (4.15 g) was added slowly into a solution containing 16 g of myristyltrimethylammonium bromide ($C_{14}TMABr$) in 100 g of water. Tetramethylammonium silicate (100 g-10% $SiO_2$), HiSil (25 g) and tetramethylammonium hydroxide (14.2 g-25% solution) were then added to the mixture. The mixture was crystallized in an autoclave at 120° C. with stirring for 24 hours.

Figure 9:
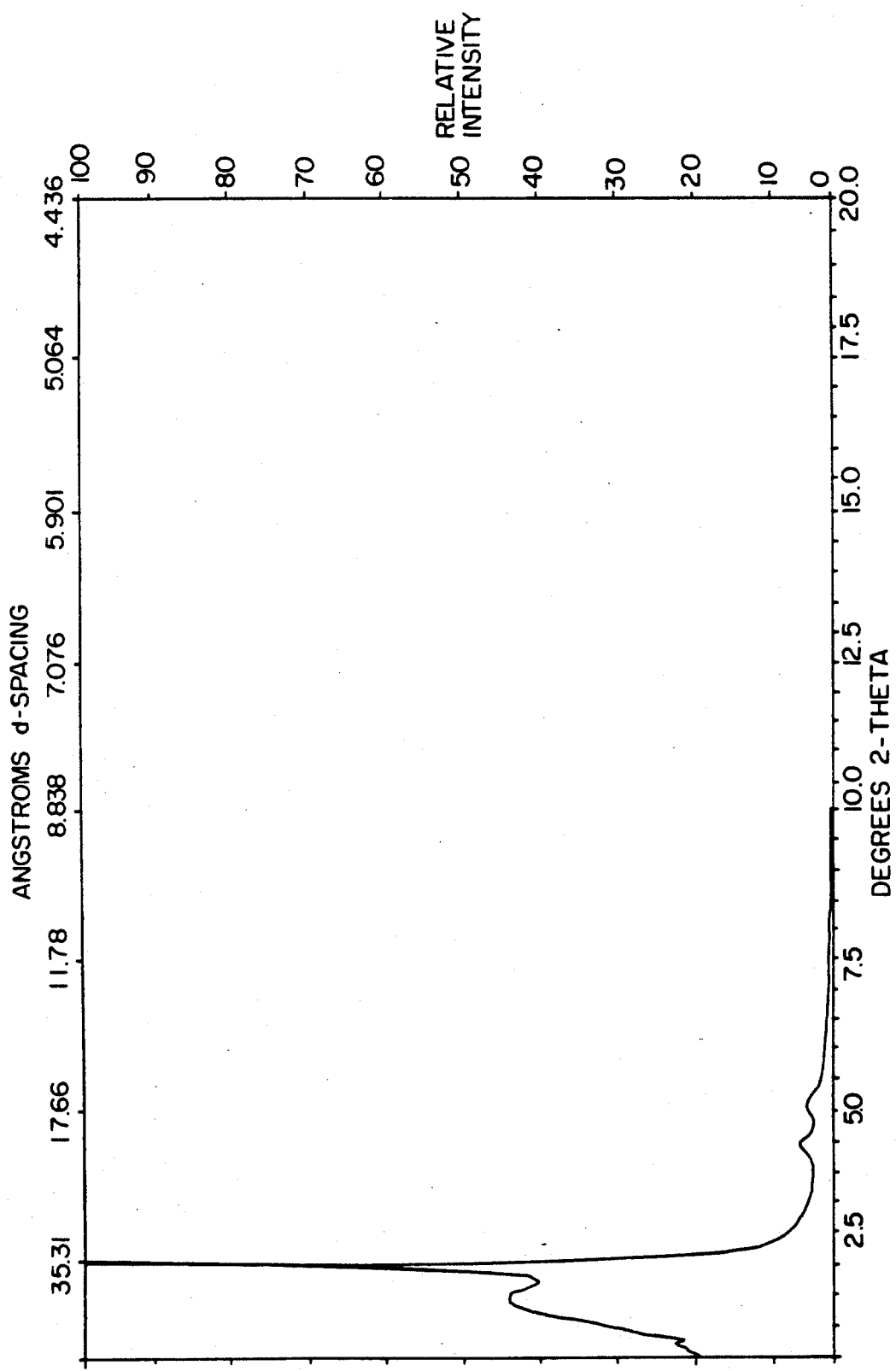

The product was filtered, washed and air dried. Elemental analysis showed the product contained 53.3 wt % $SiO_2$, 3.2 wt % $Al_2O_3$, 15.0 wt % C, 1.88 wt % N, 0.11 wt % Na and 53.5 wt % ash at 1000° C. FIG. 9 shows the X-ray diffraction pattern of the material having been calcined at 540° C. for 1 hour in $N_2$ and 6 hours in air. The X-ray diffraction pattern includes a very strong relative intensity line at 35.3±2.0 Angstroms d-spacing and weak lines at 20.4±1.0 and 17.7±1.0 Angstroms d-spacing. TEM indicated that the product contained the present ultra-large pore material.

The washed product, having been exchanged with 1N ammonium nitrate solution at room temperature, then calcined, proved to have a surface area of 827 $m^2/g$ and the following equilibrium adsorption capacities in g/100 g anhydrous sorbent:

| | |
|---|---|
| $H_2O$ | 30.8 |
| Cyclohexane | 33.0 |
| n-Hexane | 27.9 |
| Benzene | 40.7 |

EXAMPLE 10

Sodium aluminate (4.15 g) was added slowly into a solution containing 480 g of dodecyltrimethylammonium hydroxide ($C_{12}TMAOH$, 50%) solution diluted with 120 g of water. UltraSil (50 g) and an aqueous solution of tetramethylammonium silicate (200 g-10% $SiO_2$) and tetramethylammonium hydroxide (26.38 g-25% solution) were then added to the mixture. The mixture was crystallized in an autoclave at 100° C. with stirring for 24 hours.

Figure 10:
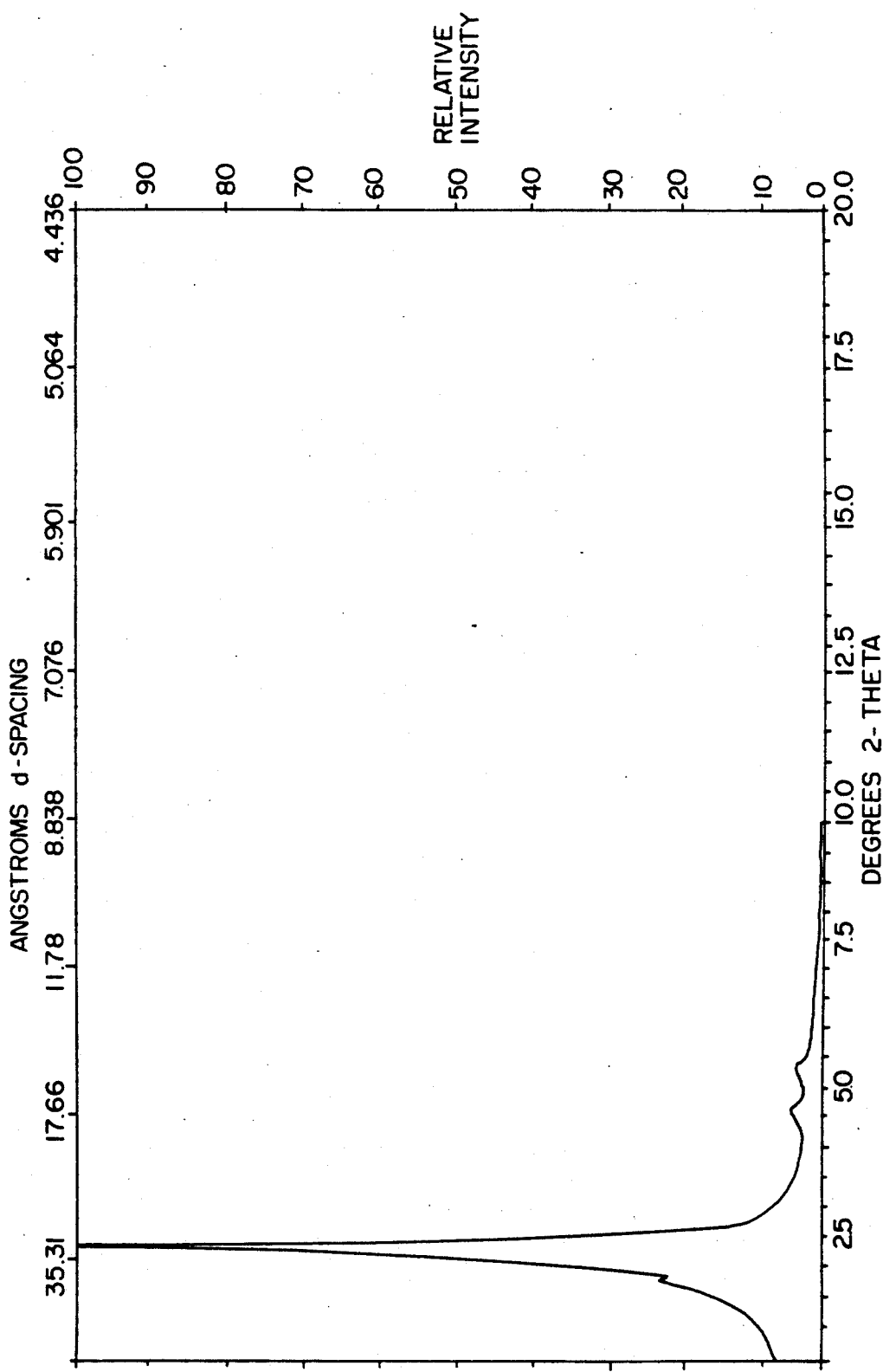

The product was filtered, washed and air dried. FIG. 10 shows the X-ray diffraction pattern of the material having been calcined at 540° C. for 1 hour in $N_2$ and 6 hours in air. The X-ray diffraction pattern includes a very strong relative intensity line at 30.4±1.5 Angstroms d-spacing and weak lines at 17.7±1.0 and 15.3±1.0 Angstroms d-spacing. TEM indicated that the product contained the present ultra-large pore material.

The washed product, having been exchanged with 1N ammonium nitrate solution at room temperature, then calcined, proved to have a surface area of 1,078 $m^2/g$ and the following equilibrium adsorption capacities in g/100 g anhydrous sorbent:

| | |
|---|---|
| $H_2O$ | 32.6 |
| Cyclohexane | 38.1 |
| n-Hexane | 33.3 |
| Benzene | 42.9 |

EXAMPLE 11

A solution of 4.9 grams of $NaAlO_2$ (43.5% $Al_2O_3$, 30% $NaO_2$) in 37.5 grams of water was mixed with 46.3 cc of 40% aqueous tetraethylammonium hydroxide solution and 96 grams of colloidal silica (40%, Ludox HS-40). The gel was stirred vigorously for 0.5 hour, mixed with an equal volume (150 ml) of cetyltrimethylammonium hydroxide solution prepared as in Example 1 and reacted at 100° C. for 168 hours. The mixture had the following composition in terms of moles per mole $Al_2O_3$:

1.1 moles $Na_2O$
30.6 moles $SiO_2$
3.0 moles $(TEA)_2O$
3.25 moles $(CTMA)_2O$
609 moles $H_2O$ The resulting solid product was recovered by filtration, washed with water then calcined at 540° C. for 16 hours in air.

The calcined product proved to have a surface area of 1,352 $m^2/g$ and the following equilibrium adsorption capacities in grams/100 grams:

| | |
|---|---|
| $H_2O$ | 23.6 |
| Cyclohexane | >50 |
| n-Hexane | 49 |
| Benzene | 67.5 |

Figure 11:
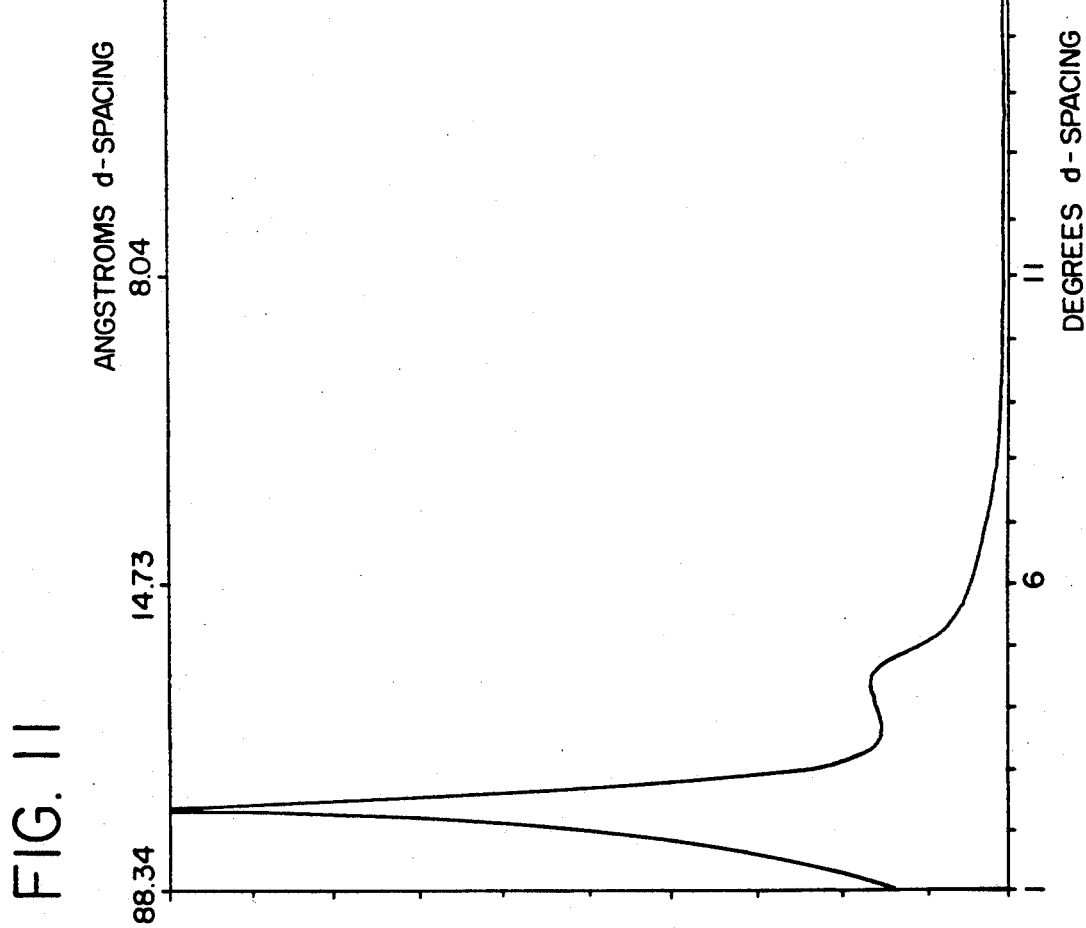

The X-ray diffraction pattern of the calcined product of this example is shown in FIG. 11. The product of this example may be characterized as including a very strong relative intensity line at 38.5±2.0 Angstroms d-spacing and a weak line at 20.3±1.0 Angstroms. TEM indicated that the product contained the present ultra-large pore material.

EXAMPLE 12

Figure 12:
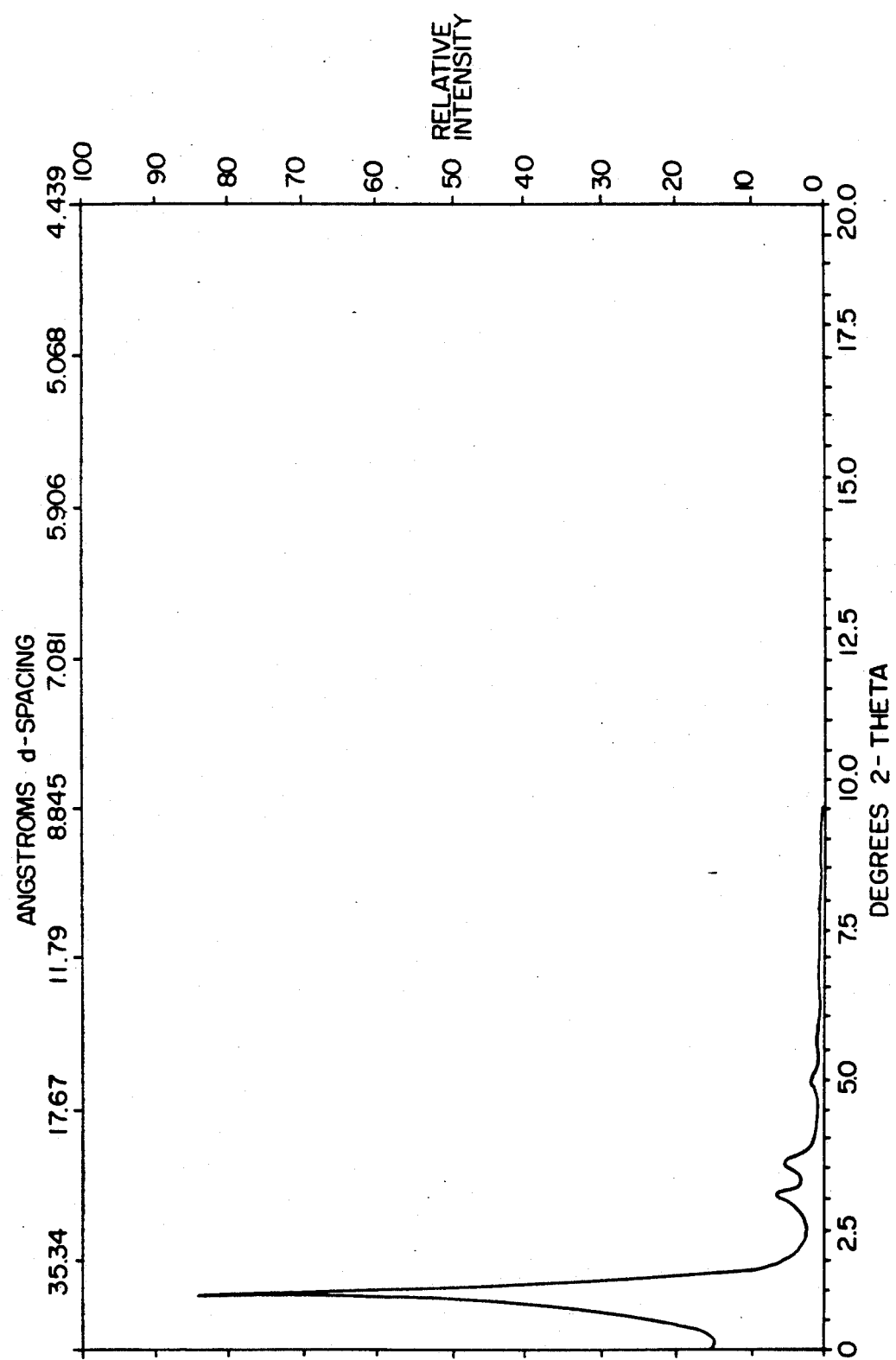

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution 10% silica) with stirring. Twenty-five grams of HiSil, a precipitated hydrated silica containing about 6 wt. % free water and about 4. wt. % bound water of hydration and having an ultimate particle size of about 0.02 micron, was added. The resulting mixture was placed in a static autoclave at 150° C. for 24 hours. The mixture had a composition in terms of moles per mole $Al_2O_3$:

1.25 moles $Na_2O$
27.8 moles $SiO_2$
5.1 moles $(CTMA)_2O$
4.40 moles $(TMA)_2O$
650 moles $H_2O$ The resulting solid product was recovered by filtration and dried in air at ambient temperature. The product was then calcined at 540° C. for 1 hour in nitrogen, followed by 6 hours in air. TEM indicated that this product contained the present ultra-large pore material. The X-ray diffraction pattern of the calcined product of this example is shown in FIG. 12. This pattern can be characterized as including a very strong relative intensity line at 44.2±2.0 Angstroms d-spacing and weak lines at 25.2±1.5 and 22.0±1.0 Angstroms.

The calcined product proved to have a surface area of 932 m²/g and the following equilibrium adsorption capacities in grams/100 grams:

| | |
|---|---|
| H₂O | 39.3 |
| Cyclohexane | 46.6 |
| n-Hexane | 37.5 |
| Benzene | 50 |

The product of this example was then ammonium exchanged with 1 N NH₄NO₃ solution, followed by calcination at 540° C. for hours in air.

EXAMPLE 13

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a steam box at 100° C. for 48 hours. The mixture had a composition in terms of moles per mole Al₂O₃:

1.25 moles Na₂O
27.8 moles SiO₂
5.1 moles (CTMA)₂O
4.4 moles (TMA)₂O
650 moles H₂O The resulting solid product was recovered by filtration and dried in air at ambient temperature. The product was then calcined at 540° C. for 1 hour in nitrogen, followed by 6 hours in air.

The calcined product proved to have the following equilibrium adsorption capacities in grams/100 grams:

| | |
|---|---|
| H₂O | 35.2 |
| Cyclohexane | >50 |
| n-Hexane | 40.8 |
| Benzene | 53.5 |

Figure 13:
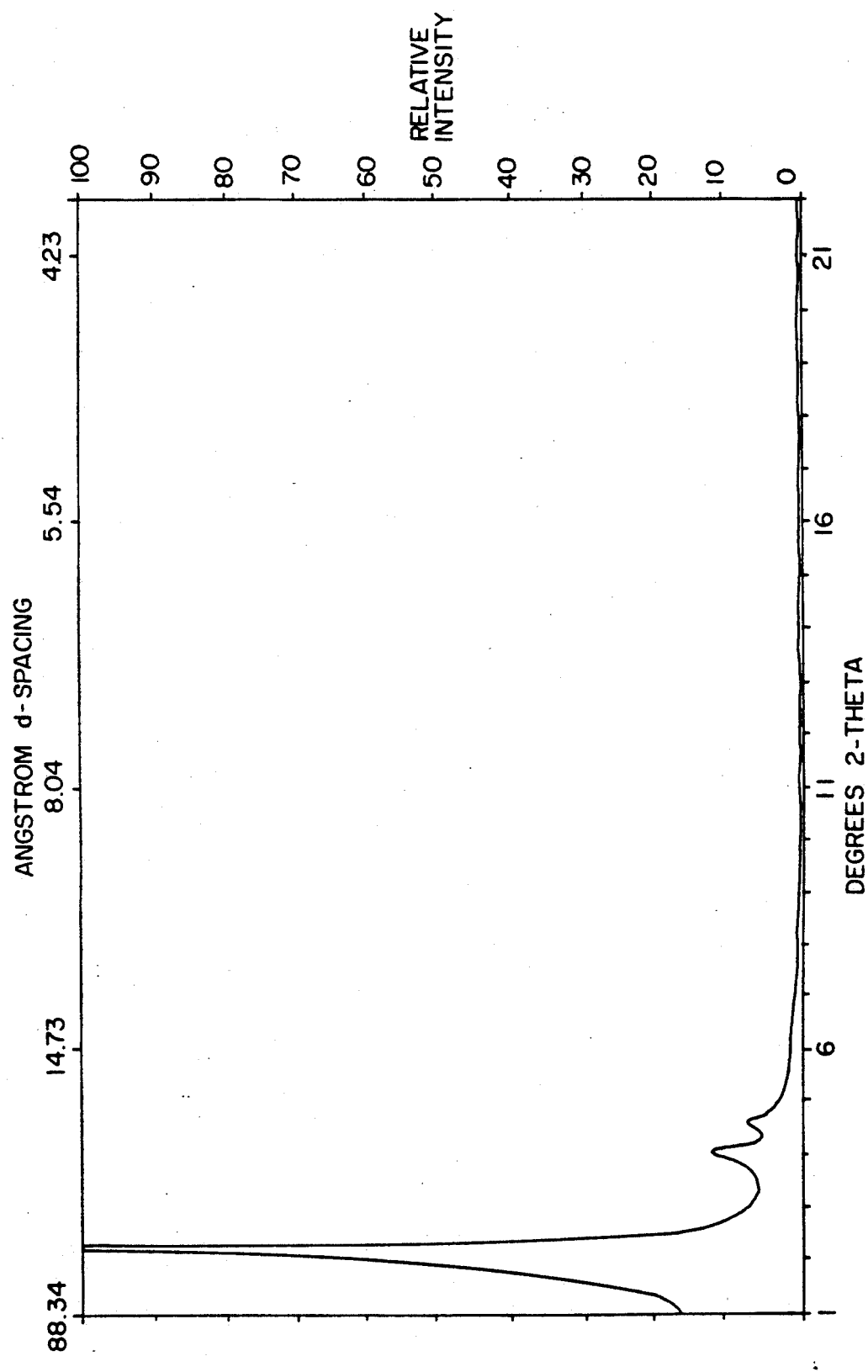

The X-ray diffraction pattern of the calcined product of this example is shown in FIG. 13. This product may be characterized as including a very strong relative intensity line at 39.1±2.0 Angstroms d-spacing and weak lines at 22.4±1.0 and 19.4±1.0 Angstroms. TEM indicated that this product contained the present ultra-large pore material.

The product of this example was then ammonium exchanged with 1 N NH₄NO₃ solution, followed by calcination at 540° C. for hours in air.

EXAMPLE 14

A mixture of 125 grams of 29% CTMA chloride aqueous solution, 200 grams of water, 3 grams of sodium aluminate (in 50 grams H₂O), 65 grams of Ultrasil, amorphous precipitated silica available from PQ Corporation, and 21 grams NaOH (in 50 grams H₂O) was stirred thoroughly and crystallized at 150° C. for 168 hours. The reaction mixture had the following relative molar composition in terms of moles per mole silica:

0.10 moles (CTMA)₂O
21.89 moles H₂O
0.036 moles NaAlO₂
0.53 moles NaOH

The solid product was isolated by filtration, washed with water, dried for 16 hours at room temperature and calcined at 540° C. for 10 hours in air.

The calcined product proved to have a surface area of 840 m²/g, and the following equilibrium adsorption capacities in grams/100 grams:

| | |
|---|---|
| H₂O | 15.2 |
| Cyclohexane | 42.0 |
| n-Hexane | 26.5 |
| Benzene | 62 |

Figure 14:
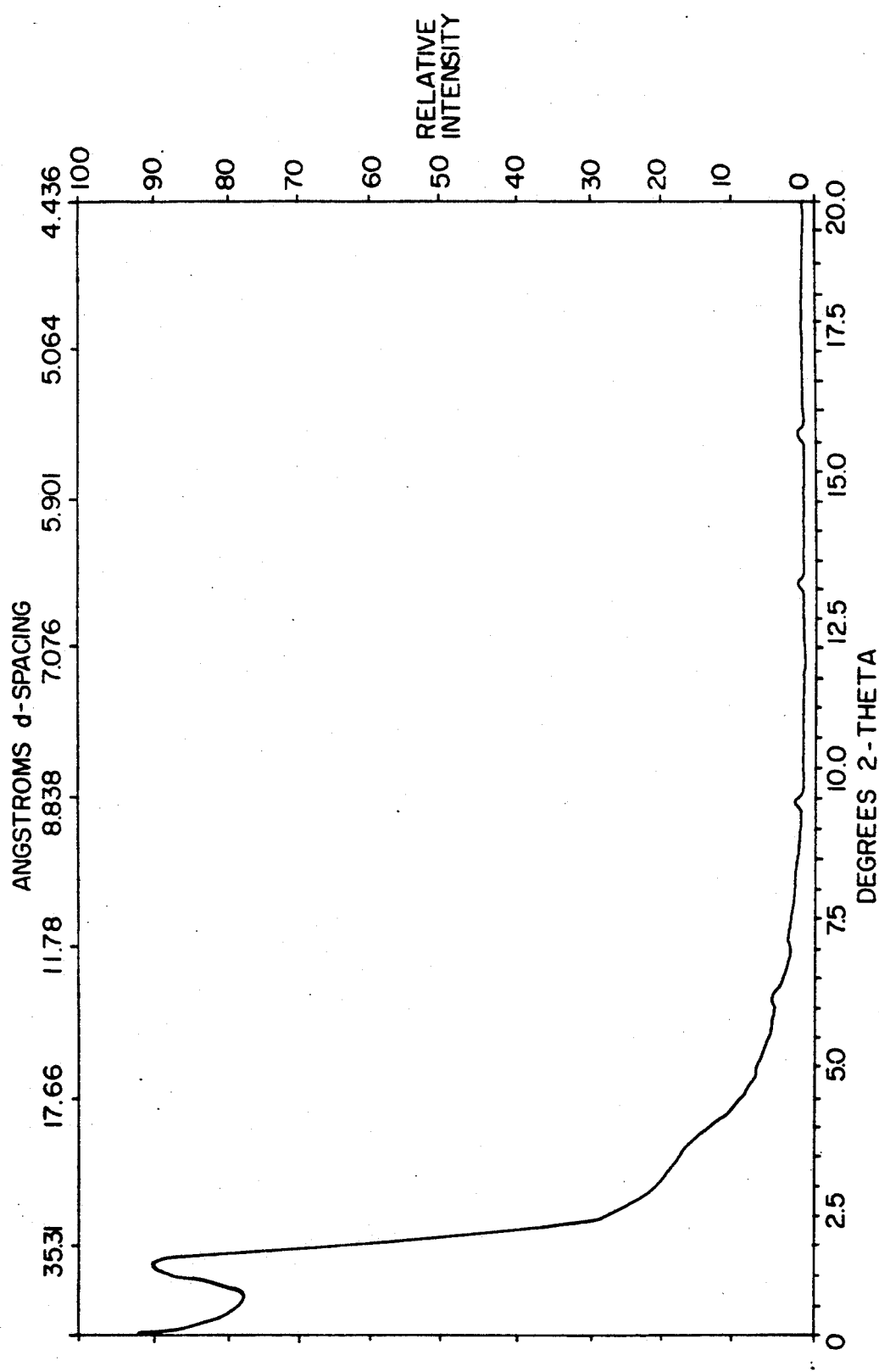

The X-ray diffraction pattern of the calcined product of this Example, shown in FIG. 14, may be characterized as including a very strong relative intensity line at 40.5±2.0 Angstroms d-spacing. TEM indicated that the product contained the present ultra-large pore material.

EXAMPLE 15

For comparison purposes, a commercially prepared ultra-stable zeolite Y was obtained. It had a benzene equilibrium adsorption capacity of 20.7 grams/100 grams. Its X-ray diffraction pattern had all the lines of zeolite Y with its highest value peak at about 14.0 Angstroms d-spacing.

EXAMPLE 16

To make the primary template mixture for this example, 240 grams of water was added to a 92 gram solution of 50% dodecyltrimethylammonium hydroxide, 36% isopropyl alcohol and 14% water such that the mole ratio of Solvent/R₂/ₓO was 155. The mole ratio of H₂O/R₂/ₓO in this mixture was 149 and the IPA/R₂/ₓO mole ratio was 6. To the primary template mixture was added 4.15 grams of sodium aluminate, 25 grams of HiSil, 100 grams of aqueous tetramethylammonium silicate solution (10% SiO₂) and 13.2 grams of 25% aqueous tetramethylammonium hydroxide solution. The mole ratio of R₂/ₓO/(SiO₂+Al₂O₃) was 0.28 for the mixture.

This mixture was stirred at 25° C. for 1 hour. The resulting mixture was then placed in an autoclave at 100° C. and stirred at 100 rpm for 24 hours. The mixture in the autoclave had the following relative molar composition in terms of moles per mole SiO₂:

0.05 mole Na₂O
0.036 mole Al₂O₃
0.18 mole (C₁₂TMA)₂O
0.12 mole (TMA)₂O
36.0 moles H₂O
1.0 mole IPA The resulting solid product was recovered by filtration, washed with water and dried in air at ambient temperature. The product was then calcined at 540° C. for 1 hour in nitrogen, followed by 6 hours in air.

The calcined product proved to have a surface area of 1,223 m²/g and the following equilibrium adsorption capacities in grams/100 grams:

| | |
|---|---|
| H₂O | 25.5 |
| Cyclohexane | 41.1 |
| n-Hexane | 35.1 |
| Benzene | 51 |

Figure 15:
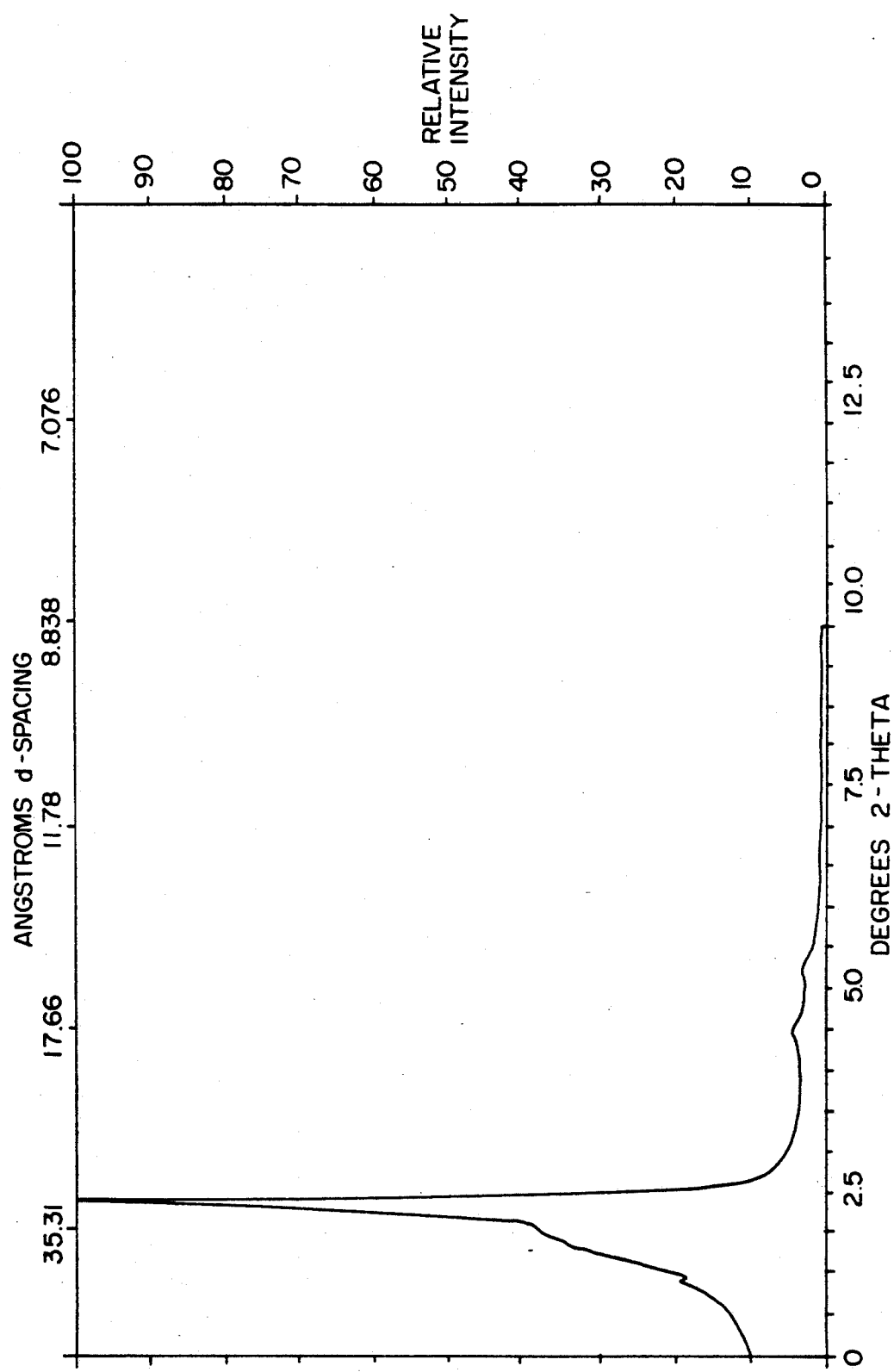

The X-ray diffraction pattern of the calcined product of this example is shown in FIG. 15. This product may be characterized as including a very strong relative intensity line at 30.8±1.5 Angstroms d-spacing and weak lines at 17.9±1.0 and 15.5±1.0 Angstroms. TEM indicated this product to contain the present ultra-large pore material.

EXAMPLE 17

A 50.75 gram quantity of decyltrimethylammonium hydroxide (prepared by contacting a ca. 29 wt. % solution of decyltrimethylammonium bromide with a hydroxide-for-halide exchange resin) was combined with 8.75 grams of tetraethylorthosilicate. The mixture was stirred for about 1 hour and then transferred to a polypropylene jar which was then placed in a steambox for about 24 hours. The mixture had a composition in terms of moles per mole $SiO_2$:

0.81 mole $(C_{10}TMA)_2O$
47.6 moles $H_2O$

The resulting solid product was filtered and washed several times with warm (60°–70° C.) distilled water and with acetone. The final product was calcined to 538° C. in $N_2$/air mixture and then held in air for about 8 hours.

The calcined product proved to have a surface area of 915 $m^2/g$ and an equilibrium benzene adsorption capacity of 35 grams/100 grams. Argon physisorption data indicated an argon uptake of 0.34 cc/gram, and a pore size of 15 Angstroms.

The X-ray diffraction pattern of the calcined product of this example may be characterized as including a very strong relative intensity line at 27.5±1.5 Angstroms d-spacing and weak lines at 15.8±1.0 and 13.7±1.0 Angstroms. TEM indicated that the product of this example contained the present ultra-large pore material.

EXAMPLE 18

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 70 grams of 1,3,5-trimethylbenzene (mesitylene). The resulting mixture was stirred at room temperature for several minutes. The gel was then loaded into a 600 cc autoclave and heated at 105° C. for sixty-eight hours with stirring at 150 rpm. The mixture had a composition in terms of moles per mole $Al_2O_3$:

1.25 moles $Na_2O$
27.8 moles $SiO_2$
5.1 moles $(CTMA)_2O$
2.24 moles $(TMA)_2O$
2,256 moles $H_2O$
80.53 moles 1,3,5-trimethylbenzene The resulting product was filtered and washed several times with warm (60°–70° C.) distilled water and with acetone. The final product was calcined to 538° C. in $N_2$/air mixture and then held in air for about 10 hours.

The calcined product proved to have an equilbrium benzene adsorption capacity of >25 grams/100 grams.

The X-ray diffraction pattern of the calcined product of this example may be characterized as including a broad, very strong relative intensity line at about 102 Angstroms d-spacing, but accurate positions of lines in the extreme low angle region of the X-ray diffraction pattern are very difficult to determine with conventional X-ray diffractometers. Furthermore, finer collimating slits were required to resolve a peak at this low 2-theta angle. The slits used in this example, starting at the X-ray tube, were 0.1, 0.3, 0.5 and 0.2 mm, respectively. TEM indicated that the product of this example contained several materials with different $d_{100}$ values as observed in their electron diffraction patterns. These materials were found to possess $d_{100}$ values between about 85 Angstroms d-spacing and about 120 Angstroms d-spacing.

EXAMPLE 19

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 120 grams of 1,3,5-trimethylbenzene (mesitylene). The resulting mixture was stirred at room temperature for several minutes. The gel was then loaded into a 600 cc autoclave and heated at 105° C. for ninety hours with stirring at 150 rpm. The mixture had a composition in terms of moles per mole $Al_2O_3$:

1.25 moles $Na_2O$
27.8 moles $SiO_2$
5.1 moles $(CTMA)_2O$
2.24 moles $(TMA)_2O$
2,256 moles $H_2O$
132.7 moles 1,3,5-trimethylbenzene The resulting product was filtered and washed several times with warm (60°–70° C.) distilled water and with acetone. The final product was calcined to 538° C. in $N_2$/air mixture and then held in air for about 10 hours.

The calcined product proved to have a surface area of 915 $m^2/g$ and an equilbrium benzene adsorption capacity of >25 grams/100 grams. Argon physisorption data indicated an argon uptake of 0.95 cc/gram, and a pore size centered on 78 Angstroms (Dollimore-Heal Method, see Example 22(b)), but running from 70 to greater than 105 Angstoms.

The X-ray diffraction pattern of the calcined product of this example may be characterized as having only enhanced scattered intensity in the very low angle region of the X-ray diffraction, where intensity from the transmitted incident X-ray beam is usually observed. However, TEM indicated that the product of this example contained several materials with different $d_{100}$ values as observed in their electron diffraction patterns. These materials were found to possess $d_{100}$ values between about 85 Angstroms d-spacing and about 110 Angstroms d-spacing.

EXAMPLE 20

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, and 18 grams of 1,3,5-trimethylbenzene (mesitylene). The resulting mixture was stirred at room temperature for several minutes.

The gel was then loaded into a 300 cc autoclave and heated at 105° C. for four hours with stirring at 150 rpm. The mixture had a composition in terms of moles per mole Al$_2$O$_3$:

1.25 moles Na$_2$O
27.8 moles SiO$_2$
5.1 moles (CTMA)$_2$O
2.24 moles (TMA)$_2$O
650 moles H$_2$O
19.9 moles 1,3,5-trimethylbenzene The resulting product was filtered and washed several times with warm (60°-70° C.) distilled water and with acetone. The final product was calcined to 538° C. in N$_2$/air mixture and then held in air for about 8 hours.

The calcined product proved to have a surface area of 975 m$^2$/g and an equlibrium benzene adsorption capacity of >40 grams/100 grams. Argon physisorption data indicated an argon uptake of 0.97 cc/gram, and a pore size of 63 Angstroms (Dollimore-Heal Method, see Example 22(b)), with the peak occurring at P/P$_o$=0.65.

The X-ray diffraction pattern of the calcined product of this example may be characterized as including a very strong relative intensity line at 63±5 Angstroms d-spacing and weak lines at 36.4±2.0, 31.3±1.5 Angstroms and 23.8±1.0 Angstroms d-spacing. TEM indicated that the product of this example contained the present ultra-large pore material.

EXAMPLE 21

For catalytic evaluation of the present invention, final products from Examples 1 through 15 were evaluated for dealkylation of tri-tert-butylbenzene (TBB) to di-tert butylbenzene. The present evaluation was conducted under one or both of two sets of conditions: (i) at a temperature of 225° C., weight hourly space velocity of 100 hr$^{-1}$ or (ii) at a temperature of 200° C., weight hourly space velocity of 200 hr$^{-1}$. Pressure was atmospheric. The feed was composed of 6.3/93.7 TTBB/toluene. Conversion was measured at 30 minutes on stream. The results were as follows:

| Catalyst of Example | Conversion, wt. % 225° C./100 hr$^{-1}$ | Conversion, wt. % 200° C./200 hr$^{-1}$ |
|---|---|---|
| 1 | 0 | — |
| 2 | 6.2 | — |
| 3 | 53.9 | — |
| 4 | 10.4 | — |
| 5 | 68.9 | — |
| 6 | 100.0 | — |
| 7 | 93.4 | 66.0 |
| 8 | 5.3 | — |
| 9 | — | 61.2 |
| 10 | — | 58.9 |
| 11 | 86.3 | — |
| 12 | 96.7 | — |
| 13 | 92.8 | — |
| 14 | — | 37.7 |
| 15 | 12.0 | 0 |

EXAMPLE 22(a)

Argon Physisorption For Pore Systems Up to About 60 Angstroms Diameter

To determine the pore diameters of the products of this invention with pores up to about 60 Angstroms in diameter, 0.2 gram samples of the products of Examples 1 through 17 were placed in glass sample tubes and attached to a physisorption apparatus as described in U.S. Pat. No. 4,762,010, which is incorporated herein by reference.

Figure 16:
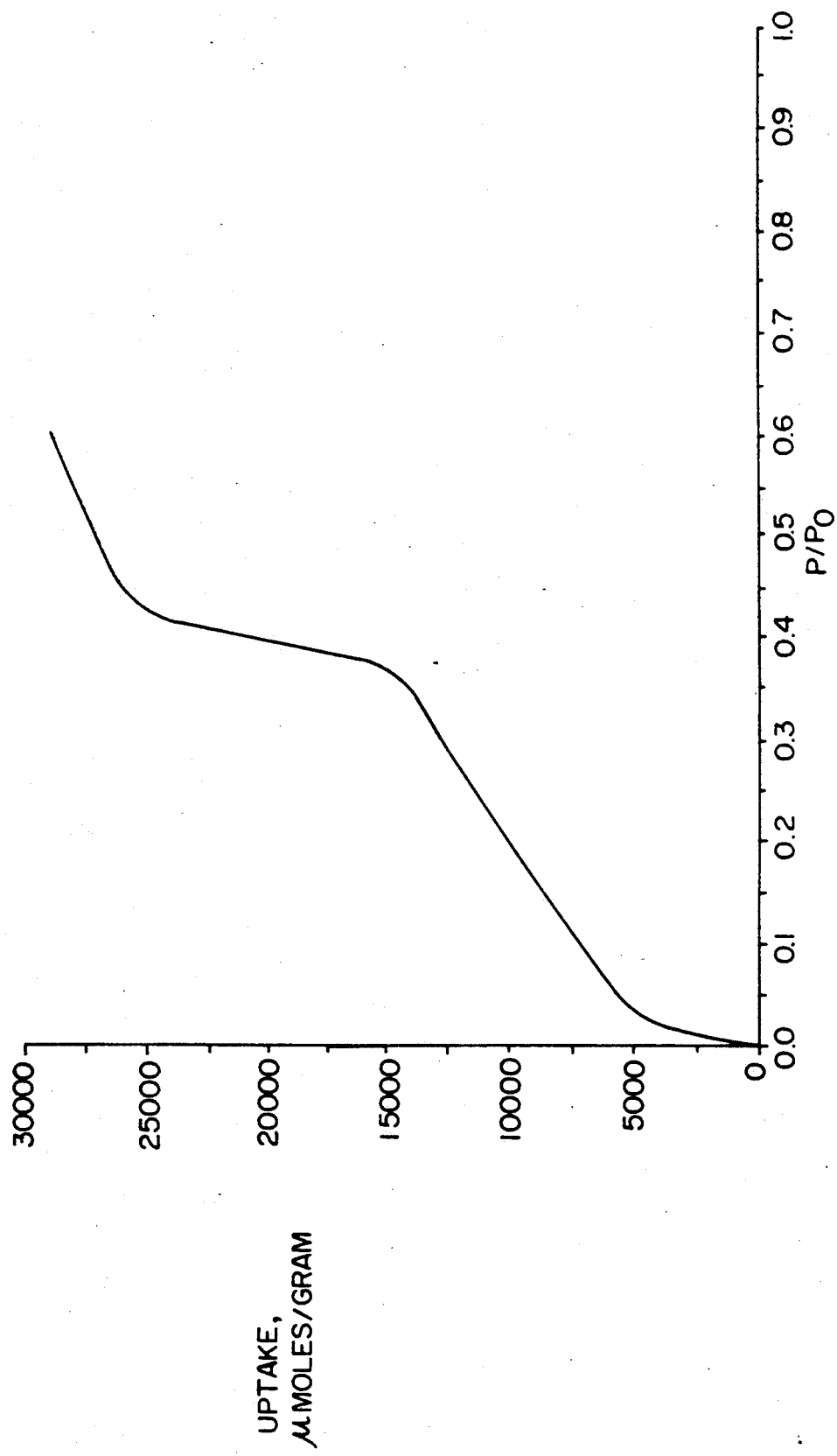
FIG. 16 is an isotherm plot of physisorption measurements from Example 22.

The samples were heated to 300° C. for 3 hours in vacuo to remove adsorbed water. Thereafter, the samples were cooled to 87° K. by immersion of the sample tubes in liquid argon. Metered amounts of gaseous argon were then admitted to the samples in stepwise manner as described in U.S. Pat. No. 4,762,010, column 20. From the amount of argon admitted to the samples and the amount of argon left in the gas space above the samples, the amount of argon adsorbed can be calculated. For this calculation, the ideal gas law and the calibrated sample volumes were used. (See also S. J. Gregg et al., *Adsorption, Surface Area and Porosity*, 2nd ed., Academic Press, 1982). In each instance, a graph of the amount adsorbed versus the relative pressure above the sample, at equilibrium, constitutes the adsorption isotherm as shown in FIG. 16 for the Example 4 product sample. It is common to use relative pressures which are obtained by forming the ratio of the equilibrium pressure and the vapor pressure P$_o$ of the adsorbate at the temperature where the isotherm is measured. Sufficiently small amounts of argon were admitted in each step to generate 168 data points in the relative pressure range from 0 to 0.6. At least about 100 points ar required to define the isotherm with sufficient detail.

Figure 17:
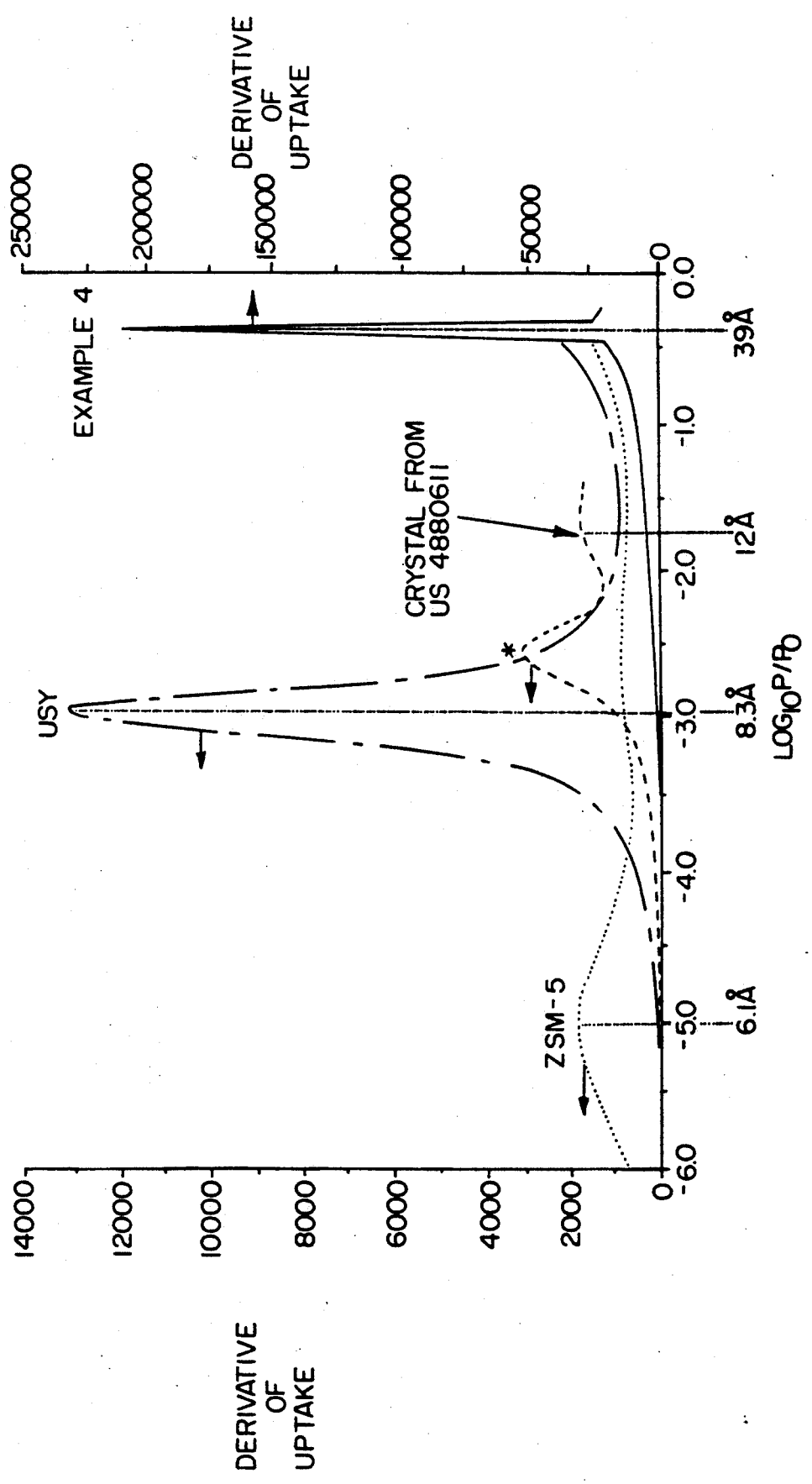
FIG. 17 is a plot of physisorption measurements from Example 22 showing pore sizes of various crystalline materials.

The step (inflection) in the isotherm, in this case (Example 4 product) at about P/P$_o$=0.4, indicates filling of a pore system. The size of the step indicates the amount adsorbed, whereas the position of the step in terms of P/P$_o$ reflects the size of the pores in which the adsorption takes place. Larger pores are filled at higher P/P$_o$. In order to better locate the position of the step in the isotherm, the derivative with respect to log (P/P$_o$) is formed. This is shown in FIG. 17. Also shown in FIG. 17 are data obtained in an identical fashion for a crystalline material from U.S. Pat. No. 4,880,611 and several other crystal materials. There is further provided a physical scale on the axis which converts the position of an adsorption peak in terms of log (P/P$_o$) to the physical pore diameter in Angstroms. This conversion was obtained by using the following formula:

$$\log(P/P_o) = \frac{K}{d - 0.38} \left( \frac{S^4}{3 (L - D/2)^3} - \frac{S^{10}}{9 (L - D/2)^9} - \frac{S^4}{3 (D/2)^3} + \frac{S^{10}}{9 (D/2)^9} \right)$$

wherein d=pore diameter in nanometers, K=32.17, S=0.2446, L=d+0.19, and D=0.57.

This formula is derived from the method of Horvath and Kawazoe (G. Horvath et al., *J. Chem. Eng. Japan*, 16 (6) 470(1983)). The constants required for the implementation of this formula were determined from a measured isotherm of ALPO-5 and its known pore size. This method is particularly useful for microporous materials having pores of up to about 60 Angstroms in diameter.

As is indicated in FIG. 17, the pore size of the material of Example 4 is 39.6 Angstroms with the peak occurring at log (P/P$_o$)=−0.4 or P/P$_o$=0.4, while the pore size of the material from U.S. Pat. No. 4,880,611 is 12 Angstroms or P/P$_o$=0.02. In the other materials, a peak is observed at P/P$_o$=0.015 which is denoted by an asterisk in FIG. 17. This peak reflects adsorption on the walls of the pores and is not otherwise indicative of the size of the pores of a given material. A value of of $P/P_o$ of 0.03 corresponds to 13 Angstroms pore size.

The results of this procedure for the samples from Examples 1 through 17 are tabulated below. The samples from Examples 10, 13 and 16 gave two separate peaks, believed to be the result of two separate ultra-large pore phases in the products.

| Examples | Pore Diameter, Angstroms |
|---|---|
| 1 | 32.2 |
| 2 | 35.4 |
| 3 | 42.5 |
| 4 | 39.6 |
| 5 | 16.9 |
| 6 | 27.3 |
| 7 | 36.6 |
| 8 | 42.6 |
| 9 | 28.3 |
| 10 | 22.8, 30.8 |
| 11 | 36.8 |
| 12 | 36.1 |
| 13 | 35.0, 42.1 |
| 14 | 40.0 |
| 15 | 8.3 |
| 16 | 22.4, 30.4 |
| 17 | 15.0 |

EXAMPLE 22(b)

Argon Physisorption For Pore Systems Over About 60 Angstroms Diameter

The above method of Horvath and Kawazoe for determining pore size from physisorption isotherms was intended to be applied to pore systems of up to 20 Angstroms diameter; but with some care as above detailed, its use can be extended to pores of up to 60 Angstroms diameter.

In the pore regime above 60 Angstroms diameter, however, the Kelvin equation can be applied. It is usually given as:

$$\ln(P/P_o) = \frac{-2\gamma V}{r_k RT} \cos \Theta$$

where:
- $\gamma$ = surface tension of sorbate
- $V$ = molar volume of sorbate
- $\Theta$ = contact angle (usually taken for practical reasons to be 0)
- $R$ = gas constant
- $T$ = absolute temperature
- $r_k$ = capillary condensate (pore) radius
- $P/P_o$ = relative pressure (taken from the physisorption isotherm)

The Kelvin equation treats adsorption in pore systems as a capillary condensation phenomenon and relates the pressure at which adsorption takes place to the pore diameter through the surface tension and contact angle of the adsorbate (in this case, argon). The principles upon which the Kelvin equation are based are valid for pores in the size range 50 to 1,000 Angstrom diameter. Below this range the equation no longer reflects physical reality, since true capillary condensation cannot occur in smaller pores; above this range the logarithmic nature of the equation precludes obtaining sufficient accuracy for pore size determination.

The particular implementation of the Kelvin equation often chosen for measurement of pore size is that reported by Dollimore and Heal (D. Dollimore and G. R. Heal, *J. Applied Chem*, 14, 108 (1964)). This method corrects for the effects of the surface layer of adsorbate on the pore wall, of which the Kelvin equation proper does not take account, and thus provides a more accurate measurement of pore diameter. While the method of Dollimore and Heal was derived for use on desorption isotherms, it can be applied equally well to adsorption isotherms by simply inverting the data set.

The products of Examples 19 and 20 were subjected to the Dollimore and Heal Method for argon physisorption data, as indicated.

EXAMPLE 23

Transmission Electron Microscopy

To further illustrate the nature of the crystalline product of this invention, samples of the products from Examples 1 through 14 and 16 through 20 were studied by transmission electron microscopy (TEM) as noted above. TEM is a technique used to reveal the microscopic structure of materials, including crystalline materials.

In order to illuminate the microstructure of materials, samples must be thin enough for an electron beam to pass through them, generally about 500-1,000 Angstrom units or so thick. The crystal morphology of the present materials usually required that they be prepared for study by ultramicrotomy. While time consuming, this technique of sample preparation is quite familiar to those skilled in the art of electron microscopy. The materials are embedded in a resin, in this case a commercially available low viscosity acrylic resin L.R. WHITE (hard), which is then cured at about 80° C. for about 1½ hours. Thin sections of the block are cut on an ultramicrotome using a diamond knife and sections in the thickness range 500-1,000 Angstrom units are collected on fine mesh electron microscope support grids. For these materials, an LKB model microtome with a 45° C. diamond knife edge was used; the support grids were 400 mesh copper grids. After evaporation of a thin carbon coating on the sample to prevent charging in the microscope (light gray color on a white sheet of paper next to the sample in the evaporator), the samples are ready for examination in the TEM.

High resolution TEM micrographs show projections of structure along the direction that the sample is viewed. For this reason, it is necessary to have a sample in specific orientations to see certain details of the microstructure of the material. For crystalline materials, these orientations are most easily chosen by observing the electron diffraction pattern (EDP) that is produced simultaneously with the electron microscope image. Such EDP's are readily produced on modern TEM instruments using, e.g. the selected area field limiting aperture technique familiar to those skilled in the art of electron microscopy. When an EDP with the desired arrangement of diffraction spots is observed, the corresponding image of the crystal giving that EDP will reveal details of the microstructure along the direction of projection indicated by the EDP. In this way, different projections of a crystal's structure ca be observed and identified using TEM.

Figure 18:
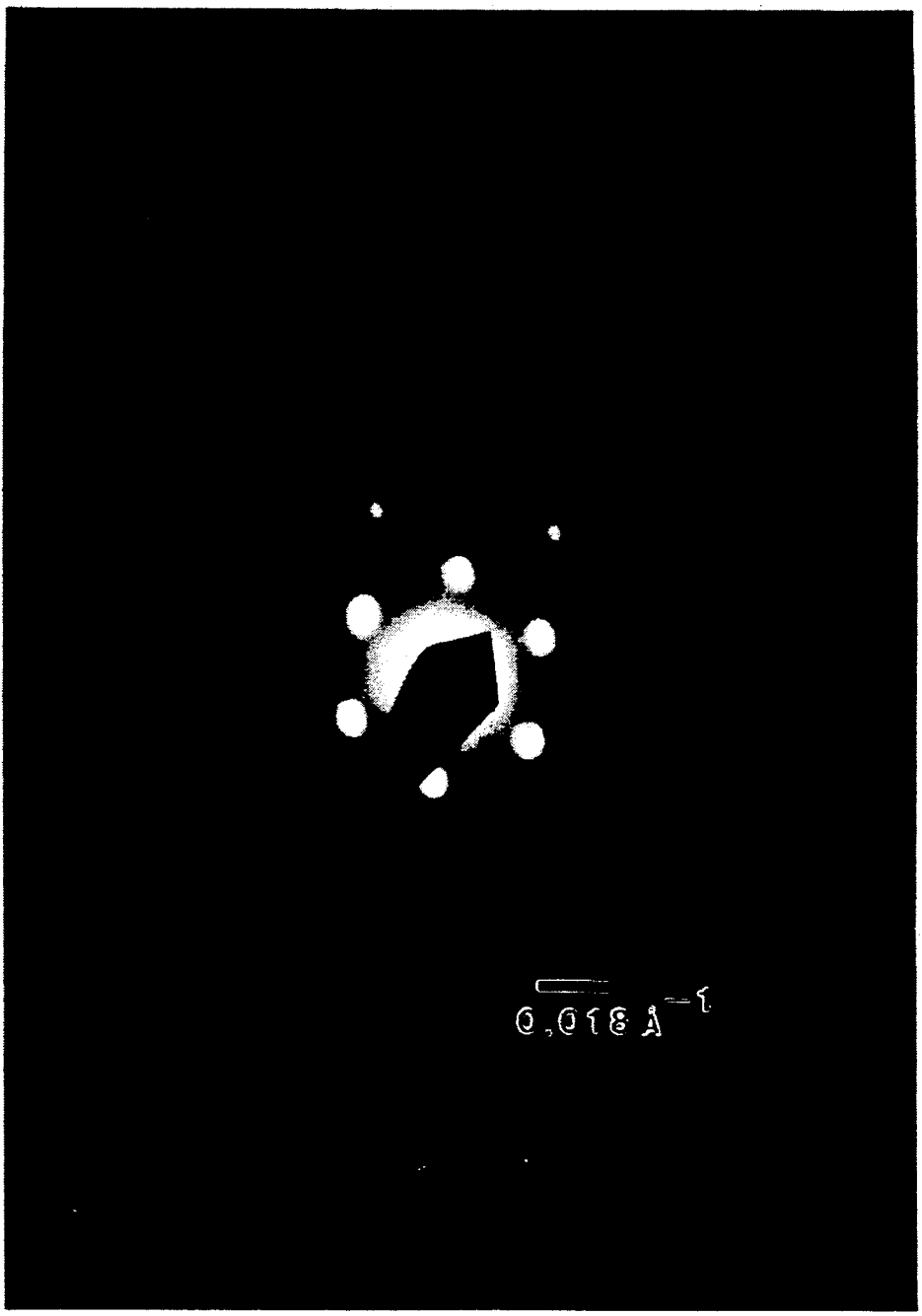
FIG. 18 is an electron diffraction pattern of the product of Example 4.

In order to observe the salient features of the crystalline product of the present invention, it is necessary to view the material in an orientation wherein the corresponding EDP gives a hexagonal arrangement of diffraction spots from a single individual crystal. If multiple crystals are present within the field limiting aperture, overlapping diffraction patterns will occur that can be quite difficult to interpret. An example of a hexagonal pattern from an individual crystal from the product in Example 4 is shown in FIG. 18. The number of diffraction spots observed depends to a degree upon the regularity of the crystalline arrangement in the material, among other things. At the very least, however, the inner ring of bright spots should be observed to obtain a good image. Individual crystals can be manipulated by specimen tilt adjustments on the TEM until this orientation is achieved. More often, it is easier to take advantage of the fact that the specimen contains many randomly oriented crystals and to simply search through the sample until a crystal giving the desired EDP (and hence orientation) is located. This latter technique was used to produce the electron micrographs discussed below.

Microtomed samples of materials from the Examples were examined by the techniques described above in a JEOL 200 CX transmission electron microscope operated at 200,000 volts with an effective 2 Angstrom objective aperture in place. The instrument has a point-to-point resolution of 4.5 Angstroms. Other experimental arrangements familiar to one skilled in the art of high resolution (phase contrast) TEM could be used to produce equivalent images provided care is taken to keep the objective lens on the underfocus (weak leans) side of the minimum contrast lens current setting. FIG. 19 is an electron micrograph from a microtomed thin section of the crystalline product from Example 4. This micrograph shows a reasonably regular array of large channels in a hexagonal arrangement. The repeat distance between the channels is about 45 Angstrom units, which is consistent with the position of the first peak in the X-ray diffraction pattern (41 Angstroms/$\sqrt{3/2}$) of this material. Since the channels must have walls between them, this observation is also consistent with the estimated pore size of about 39.6 Angstrom units calculated from Argon physisorption measurements of this material in Example 17.

FIG. 20 is an electron micrograph from a microtomed thin section of the crystalline product from Example 5. This micrograph shows a reasonably regular array of somewhat smaller channels in a hexagonal arrangement. The repeat distance between the channels is about 30 Angstrom units, which is consistent with the position of the first peak in the X-ray diffraction pattern (25 Angstroms/$\sqrt{3/2}$) of this material. The smaller pore size of this material was also verified by Argon physisorption measurements reported in Example 22(a), where a value of 16.9 Angstrom units was calculated for the material in Example 5.

FIG. 21 is an electron micrograph from a microtomed thin section of the crystalline product from Example 19. The channels in this image are quite large and rather irregular, but the characteristic hexagonal arrangement of the material of the present invention is evident.

EXAMPLES 24-26

The material of Example 11 was evaluated for isoparaffin:olefin alkylation activity in the presence of a Lewis acid. In the standard start-up procedure, 10 grams of catalyst were placed in a 300 cc reactor, and about 300 cc of isobutane were charged to fill the reactor. When the resulting mixture was cooled to the desired temperature with constant stirring at 1,500–1,900 rpm, $BF_3$ gas was introduced to the reactor. After $BF_3$ breakthrough was observed, the $BF_3$ flow rate was then reduced to a level equivalent to 2-3 wt. % of total hydrocarbons processed. At this point, a pre-mixed 10/1 wt/wt isobutane/2-butene mixture was continuously fed into the reactor to initiate alkylation. The operating conditions were 150 psig, 50° F., 1,500–1,900 rpm, 1.3 WHSV based on olefin and 2-3 wt. % $BF_3$ based on total hydrocarbon feed. Reactor effluent was continuously withdrawn through a back pressure regulator and then sent to a receiver which was maintained at 0° C. and atmospheric pressure. Periodically, the product was drained from the receiver and weathered at room temperature prior to analysis.

A liquid on-line gas chromatograph coupled with an automatic sampling device was employed to monitor the course of the alkylation reaction. All of the samples (on-line, gas and liquid) were analyzed by a fused silica capillary column (Durabond DB-1 available from the Alltech Company of Deerfield, Ill.). All reported octane numbers are measured values.

EXAMPLE 24

| ALKYLATION OF ISOBUTANE/2-BUTENE FEED | | | |
|---|---|---|---|
| Reaction Conditions | | | |
| Reactor Temperature (F.°) | | 50 | |
| Reactor Pressure (psig) | | 150 | |
| Olefin WHSV ($hr^{-1}$) | | 1.3 | |
| $BF_3$ Cofeed Rate (wt. %) | | 2.0 | |
| Feed Composition, wt. % | | | |
| 2-Butene | | 9.3 | |
| Isobutane | | 90.3 | |
| n-paraffins | | 0.4 | |
| Time On-Stream, hrs | 4 | 24 | 48 |
| Product Composition, wt. % | | | |
| $C_5$—$C_7$ | 4.8 | 8.2 | 9.6 |
| $C_8$'s | 87.2 | 82.8 | 76.4 |
| $C_9+$ | 8.0 | 9.0 | 14.0 |
| TMP/DMH* | 7.9 | 4.8 | 4.6 |
| Octanes | | | |
| R + O | — | 96.0 | 95.9 |
| M + O | — | 94.9 | 94.2 |
| R + M/2 | — | 95.5 | 95.0 |

*Ratio of high octane trimethylpentanes (TMP) to lower octane dimethylhexanes (DMH)

EXAMPLES 25 AND 26

| | COMPARISON OF THE MATERIAL OF EXAMPLE WITH SILICA CATALYST, BOTH USING $BF_3$ PROMOTER | |
|---|---|---|
| Catalyst | Material of Example 11 Promoted With $BF_3$ | $BF_3/SiO_2$ |
| Reaction Conditions | | |
| Reactor Temperature (°F.) | 50 | 50 |
| Time On-Stream (Hrs) | 24 | 20 |
| Olefin WHSV | 1.3 | 1.3 |
| $BF_3$ Co-feed Rate (wt. %) | 2.0 | 2.0 |
| Pressure (psig) | 150 | 150 |
| Feed Composition, wt. % | | |
| 2-Butene | 9.3 | 9.3 |
| Isobutene | 90.3 | 90.3 |
| n-paraffins | 0.4 | 0.4 |
| Product Composition, wt. % | | |
| $C_5$—$C_7$ | 8.2 | 10.4 |
| $C_8$'s | 82.8 | 82.2 |
| $C_9+$ | 9.0 | 7.4 |
| TMP/DMH | 4.8 | 4.3 |
| $C_5$ + Octanes | | |
| R + O | 96.0 | 95.5 |
| M + O | 94.9 | 93.5 |

COMPARISON OF THE MATERIAL OF EXAMPLE
WITH SILICA CATALYST, BOTH USING BF₃ PROMOTER

| Catalyst | Material of Example 11 Promoted With BF₃ | BF₃/SiO₂ |
|---|---|---|
| R + M/2 | 95.5 | 94.5 |

Changes and modifications in the specifically described embodiments can be carried out without departing from the scope of the invention which is intended to be limited only by the scope of the appended claims.

We claim:

1. A process for alkylating an isoparaffin with an olefin comprising contacting an isoparaffin having from 4 to 8 carbon atoms with an olefin having from 2 to 12 carbon atoms in an alkylation reaction zone at temperature from about −20° C. to about 150° C. with an alkylation catalyst complex comprising a Lewis acid and an inorganic, porous crystalline phase material having, after calcination, a hexagonal arrangement of uniformly-sized pores having diameters of at least about 13 Angstrom Units and exhibiting a hexagonal electron diffraction pattern that can be indexed with a $d_{100}$ value greater than about 18 Angstrom Units, wherein the molar ratio of said isoparaffin to said olefin is from about 1 to about 250 to evolve a product stream containing $C_5+$ alkylate.

2. The process of claim 1 wherein said crystalline phase has an X-ray diffraction pattern following calcination with at least one peak whose d-spacing corresponds to the $d_{100}$ value from the electron diffraction pattern.

3. The process of claim 1 wherein said crystalline phase exhibits a benzene adsorption capacity of greater than about 15 grams benzene per 100 grams at 50 torr and 25° C.

4. The process of claim 1 wherein said crystalline phase has a composition expressed as follows:

$$M_{n/q}(W_aX_bY_cZ_dO_h)$$

wherein M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and (a+b+c+d)=1.

5. The process of claim 4 wherein the sum (a+b+c) is greater than d, and h=2.

6. The process of claim 4 wherein W comprises a divalent first row transition metal or magnesium; X comprises aluminum, boron, gallium or iron; Y comprises silicon or germanium; and Z comprises phosphorus.

7. The process of claim 4 wherein W comprises cobalt, X comprises aluminum, Y comprises silicon and Z comprises phosphorus.

8. The process of claim 5 wherein W comprises a divalent first row transition metal or magnesium; X comprises aluminum, boron, gallium or iron; Y comprises silicon or germanium; and Z comprises phosphorus.

9. The process of claim 5 wherein W comprises cobalt, X comprises aluminum, Y comprises silicon and Z comprises phosphorus.

10. The process of claim 4 wherein a and d are 0 and h=2.

11. The process of claim 10 wherein X comprises aluminum, boron, gallium or iron and Y comprises silicon or germanium.

12. The process of claim 10 herein X comprises aluminum and Y comprises silicon.

13. A process for alkylating an isoparaffin with an olefin comprising contacting an isoparaffin having from 4 to 8 carbon atoms with an olefin having from 2 to 12 carbon atoms in an alkylation reaction zone at temperature from about −20° C. to about 150° C. with an alkylation catalyst complex comprising a Lewis acid and a crystalline phase material having a hexagonal arrangement of uniformly-sized pores having diameters of at least about 13 Angstrom Units, and a composition, expressed on an anhydrous basis as follows:

$$rRM_{n/q}(W_aX_bY_cZ_dO_h)$$

wherein R is the total organic material not included in M; r is the number of moles or mole fraction of R; M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and (a+b+c+d)=1, said crystalline phase exhibiting a hexagonal electron diffraction pattern that can be indexed with a $d_{100}$ value greater than about 18 Angstrom Units.

14. The process of claim 13 wherein said crystalline phase has an X-ray diffraction pattern following calcination with at least one peak whose d-spacing corresponds to the $d_{100}$ value from the electron diffraction pattern.

15. The process of claim 13 wherein said crystalline phase exhibits a benzene adsorption capacity of greater than about 15 grams benzene per 100 grams at 50 torr and 25° C.

16. The process of claim 13 having original ions replaced, at least in part, with an ion or a mixture of ions selected from the group consisting of hydrogen and hydrogen precursors, rare earth metals, and metals of Groups IA, IIA, VIIA, VIIIA, IB, IIB, IIIB, IVB and VIIB of the Periodic Table of the Elements.

17. The process of claim 13 further comprising thermally treating said crystalline phase material.

18. The process of claim 16 further comprising thermally treating said crystalline phase material.

19. The process of claim 16 wherein said replacing ions comprise hydrogen or a hydrogen precursor.

20. The process of claim 16 wherein said replacing ions comprise metals.

21. The process of claim 1 wherein said porous crystalline phase has an X-ray diffraction pattern substantially as shown in FIG. 1.

22. The process of claim 1 wherein said porous crystalline phase has an X-ray diffraction pattern substantially as shown in FIG. 2.

23. The process of claim 1 wherein said porous crystalline phase has an X-ray diffraction pattern substantially as shown in FIG. 3.

24. The process of claim 1 wherein said porous crystalline phase has an X-ray diffraction pattern substantially as shown in FIG. 4.

25. The process of claim 1 wherein said porous crystalline phase has an X-ray diffraction pattern substantially as shown in FIG. 5.

26. The process of claim 1 wherein said porous crystalline phase has an X-ray diffraction pattern substantially as shown in FIG. 6.

27. The process of claim 1 wherein said porous crystalline phase has an X-ray diffraction pattern substantially as shown in FIG. 7.

28. The process of claim 1 wherein said porous crystalline phase has an X-ray diffraction pattern substantially as shown in FIG. 8.

29. The process of claim 1 wherein said porous crystalline phase has an X-ray diffraction pattern substantially as shown in FIG. 9.

30. The process of claim 1 wherein said porous crystalline phase has an X-ray diffraction pattern substantially as shown in FIG. 10.

31. The process of claim 1 wherein said porous crystalline phase has an X-ray diffraction pattern substantially as shown in FIG. 11.

32. The process of claim 1 wherein said porous crystalline phase has an X-ray diffraction pattern substantially as shown in FIG. 12.

33. The process of claim 1 wherein said porous crystalline phase has an X-ray diffraction pattern substantially as shown in FIG. 13.

34. The process of claim 1 wherein said porous crystalline phase has an X-ray diffraction pattern substantially as shown in FIG. 14.

35. The process of claim 1 wherein said porous crystalline phase has an X-ray diffraction pattern substantially as shown in FIG. 15.

36. A process for alkylating an isoparaffin with an olefin comprising contacting an isoparaffin having from 4 to 8 carbon atoms with an olefin having from 2 to 12 carbon atoms in an alkylation reaction zone at temperature from about $-20°$ C. to about $150°$ C. with an alkylation catalyst complex comprising a Lewis acid and an inorganic, porous crystalline phase giving an X-ray diffraction pattern following calcination with at least two peaks at positions greater than about 10 Angstrom Units d-spacing, at least one of which is at a position greater than about 18 Angstrom Units d-spacing, and no peaks at positions less than about 10 Angstrom Units d-spacing with relative intensity greater than about 20% of the strongest peak, and exhibiting a hexagonal electron diffraction pattern that can be indexed with a $d_{100}$ value greater than about 18 Angstrom Units.

37. The process of claim 36 wherein said X-ray diffraction pattern following calcination has at least one peak whose d-spacing corresponds to the $d_{100}$ value from the electron diffraction pattern.

38. The process of claim 36 wherein said crystalline phase exhibits a benzene adsorption capacity of greater than about 15 grams benzene per 100 grams at 50 torr and $25°$ C.

39. A process for alkylating an isoparaffin with an olefin comprising contacting an isoparaffin having from 4 to 8 carbon atoms with an olefin having from 2 to 12 carbon atoms in an alkylation reaction zone at temperature from about $-20°$ C. to about $150°$ C. with an alkylation catalyst complex comprising a Lewis acid and a crystalline phase having a composition, expressed on an anhydrous basis, as follows:

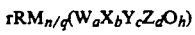

$$rRM_{n/q}(W_aX_bY_cZ_dO_h)$$

wherein R is the total organic material not included in M; r is the number of moles or mole fraction of R; M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$, said crystalline phase exhibiting an X-ray diffraction pattern following calcination with at least two peaks at positions greater than about 10 Angstrom Units d-spacing, at least one of which is at a position greater than about 18 Angstrom Units d-spacing, and no peaks at positions less than about 10 Angstrom Units d-spacing with relative intensity greater than about 20% of the strongest peak, and exhibiting a hexagonal electron diffraction pattern that can be indexed with a $d_{100}$ value greater than about 18 Angstrom Units.

40. The process of claim 34 wherein said X-ray diffraction pattern following calcination has at least one peak whose d-spacing corresponds to the $d_{100}$ value from the electron diffraction pattern.

41. The process of claim 39 wherein said crystalline phase exhibits a benzene adsorption capacity of greater than about 15 grams benzene per 100 grams at 50 torr and $25°$ C.

42. The process of claim 39 wherein said crystalline phase has original ions replaced, at least in part, with an ion or a mixture of ions selected from the group consisting of hydrogen and hydrogen precursors, rare earth metals, and metals of Groups IA, IIA, VIIA, VIIIA, IB, IIB, IIIB, IVB and VIIB of the Periodic Table of the Elements.

43. The process of claim 39 further comprising thermally treating said crystalline phase material.

44. The process of claim 42 further comprising thermally treating said crystalline phase material.

45. The process of claim 42 wherein said replacing ions comprise hydrogen or a hydrogen precursor.

46. The process of claim 42 wherein said replacing ions comprise metals.

47. The process of claim 42 wherein said crystalline phase is composited with a matrix.

48. The process of claim 47 wherein said matrix comprises alumina, silica, silica-alumina, titania, zirconia, clay or combination thereof.

49. The process of claim 1 wherein water and/or water-producing material is preintroduced into the catalyst complex.

50. The process of claim 49 wherein the amount of water preintroduced into the catalyst complex ranges from about 0.25 to about 25 percent by weight of the catalyst complex.

51. The process of claim 50 wherein the amount of water preintroduced into the catalyst complex ranges from about 1.0 to about 10 percent by weight of the catalyst complex.

52. The process of claim 1 wherein water and/or water-producing material is cofed with the reactants.

53. The process of claim 52 wherein the amount of water ranges from about 0.1 ppmw to about 1 weight percent based upon the total hydrocarbon feed rate.

54. The process of claim 1 wherein the isoparaffin contains from 4 to 6 carbon atoms and the olefin contains from 2 to 6 carbon atoms.

55. The process of claim 1 wherein the Lewis acid is selected from the group consisting of $BF_3$, $SbF_5$ and $AlCl_3$.

* * * * *